United States Patent [19]

Schneiderman

[11] Patent Number: 5,099,424
[45] Date of Patent: Mar. 24, 1992

[54] MODEL USER APPLICATION SYSTEM FOR CLINICAL DATA PROCESSING THAT TRACKS AND MONITORS A SIMULATED OUT-PATIENT MEDICAL PRACTICE USING DATA BASE MANAGEMENT SOFTWARE

[75] Inventor: Barry Schneiderman, 5 Hills Acre Pk (Snell Rd.), Lee, N.H. 03820

[73] Assignee: Barry Schneiderman, Lee, N.H.

[21] Appl. No.: 383,180

[22] Filed: Jul. 20, 1989

[51] Int. Cl.$^5$ .................... G06F 15/21; G06F 15/42
[52] U.S. Cl. ............................................. 364/413.02
[58] Field of Search ...................... 364/413.02, 413.01

[56] References Cited

U.S. PATENT DOCUMENTS 3,872,448  3/1975  Mitchell, Jr. ..................... 364/200
4,130,881  12/1978  Haessler et al. ................... 364/900
4,878,175  10/1989  Norden-Paul et al. ......... 364/413.01

OTHER PUBLICATIONS

Hewlett Packard 78707A POMS Clinical User's Guide, Manual No. 78707-91996, pp. (1-1)-(1-34), 1982 Benevolent Dictator 4.3, Information Health Network, Okemos, MI, 1985.
Button, PC-File/R User's Guide, ButtonWare, Inc., pp. 24-39 and 84-89.
"Better Care, Shorter Stays, Thanks to Networking", Data Communications, Nov. 1986.
Mowry et al., "Evaluating Automated Information Systems", Nursing Economics, vol. 5, No. 1, Jan./Feb. 1987.
Bimm, "Computers in Critical Care", Critical Care Nursing Quarterly, 9(4), pp. 53-63, 1987.
Practice Partner Patient Records, Physician Micro System, Inc., Seattle, WA 98121, 1989.

Mowry et al., "Automated Information Systems in Quality Assurance", Nursing Economics.
Korpman, "Patient Care Information Systems: Looking to the Future".
"Ulticare: A Bedside Patient Care Information System", Health Data Sciences Corporation.

Primary Examiner—Jerry Smith
Assistant Examiner—David Huntley

[57] ABSTRACT

A computer system for recording patient care results for retrospective analysis in a primary care out-patient environment provides, in the present system, for entry of separate, linked electrocardiographic (EKG) or chest x-ray (CXR) test results (or both) for a database of patients. Entry of the EKG and/or CXR results prompts the creation of a separate lab record, if not already present, which may be holding blood work from the same lab test request. Portions of information entered in the EKG or CXR routine are automatically transferred to the separate lab record. Provision is made for linking the EKG or CXR records to the lab record in both "source" and "non-source" situations; a "source" situation meaning that the lab test request was made formally during an office visit, and a "non-source" situation meaning that the lab test request was made informally, such as by telephone. Two print generation programs pull together various linked data files and selectively print out information contained therein. The first prints out EKG and/or CXR data in conjunction with other clinical observations recorded at the primary care "parent" office visit. The second prints out specialist data in conjunction with other clinical observations recorded at the primary care "parent" office visit which prompted the referrals. The present system further includes a revision of the system's specialist record from an earlier work for more explicit use in information management.

7 Claims, 30 Drawing Sheets

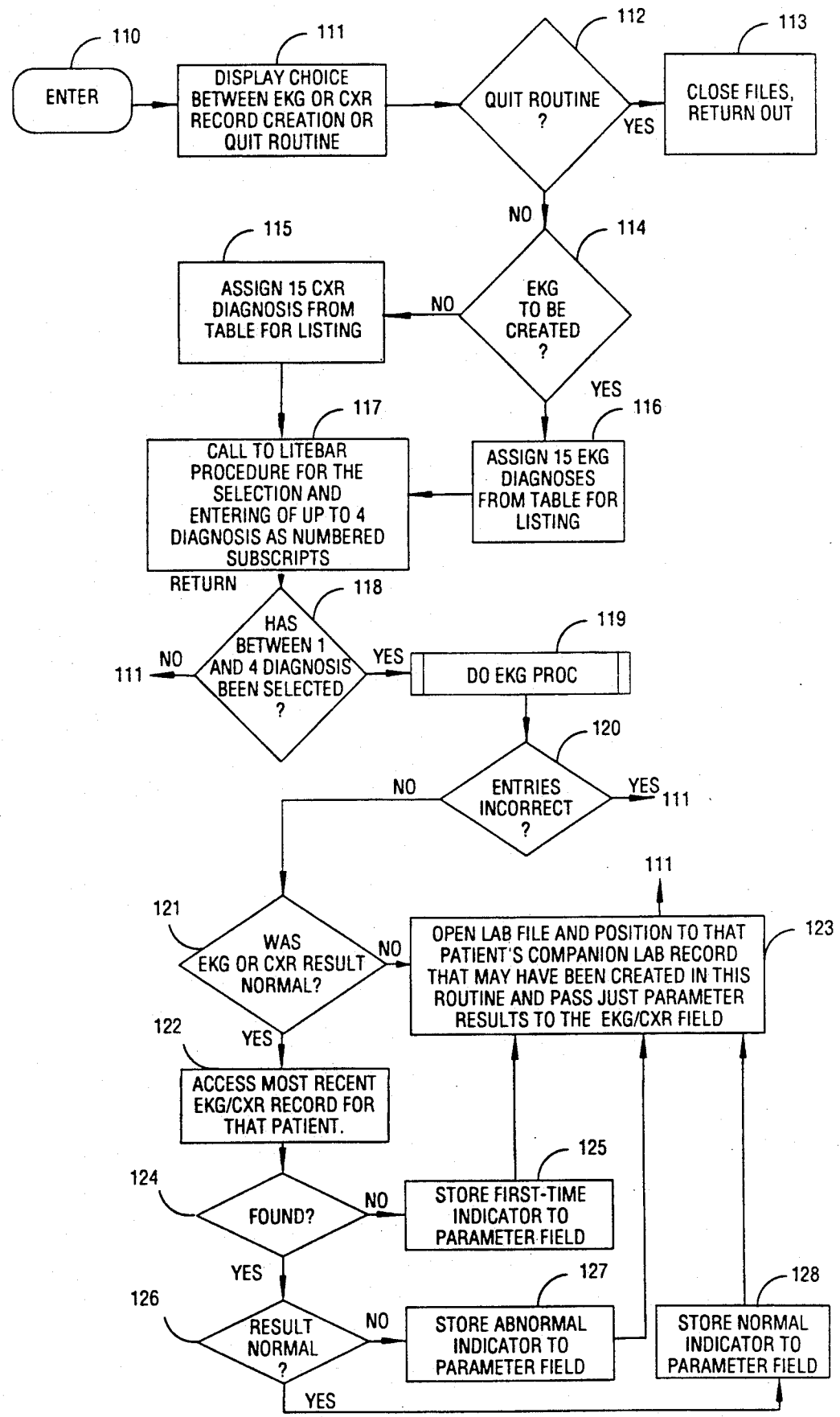
FIG. #1

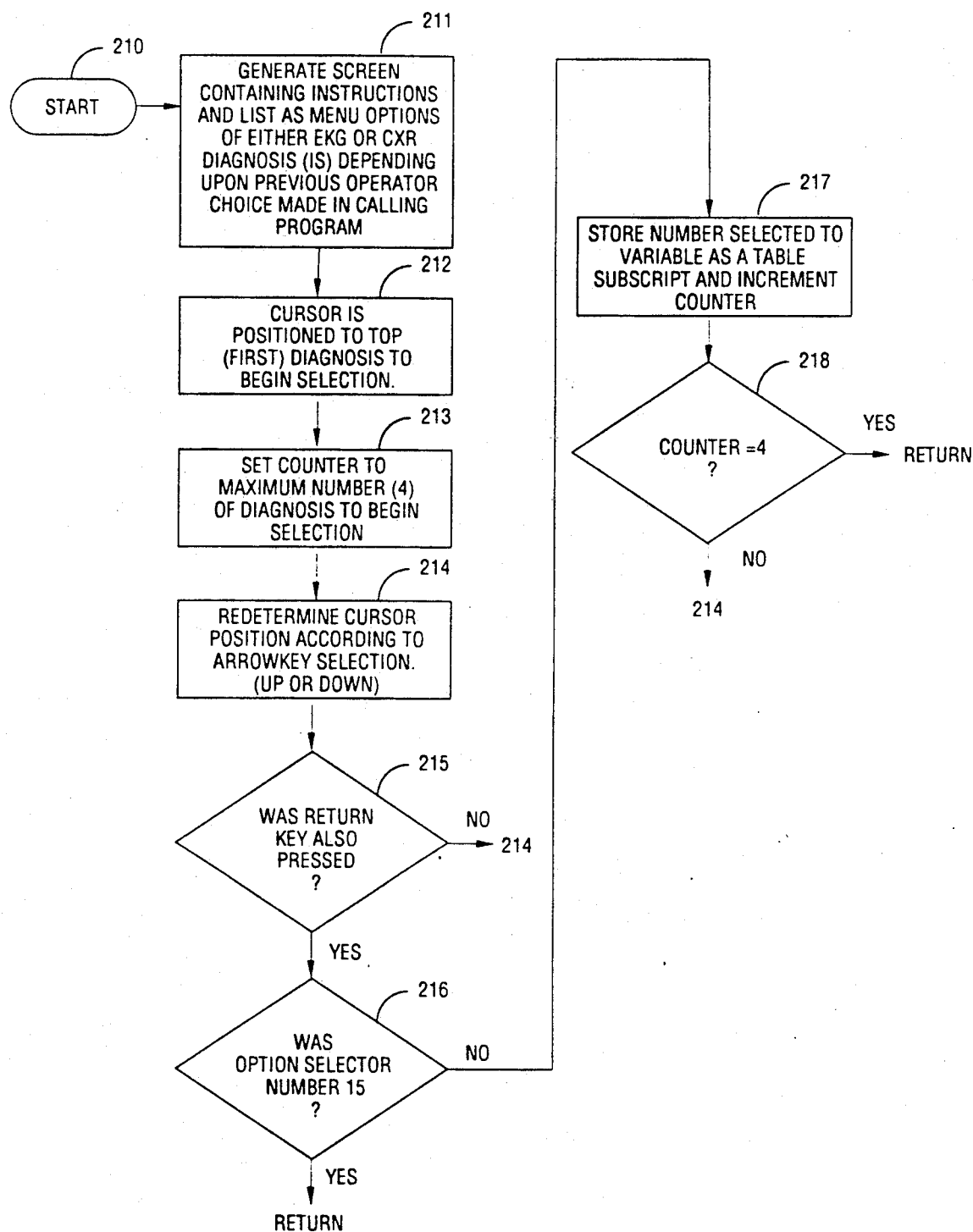
FIG. #2

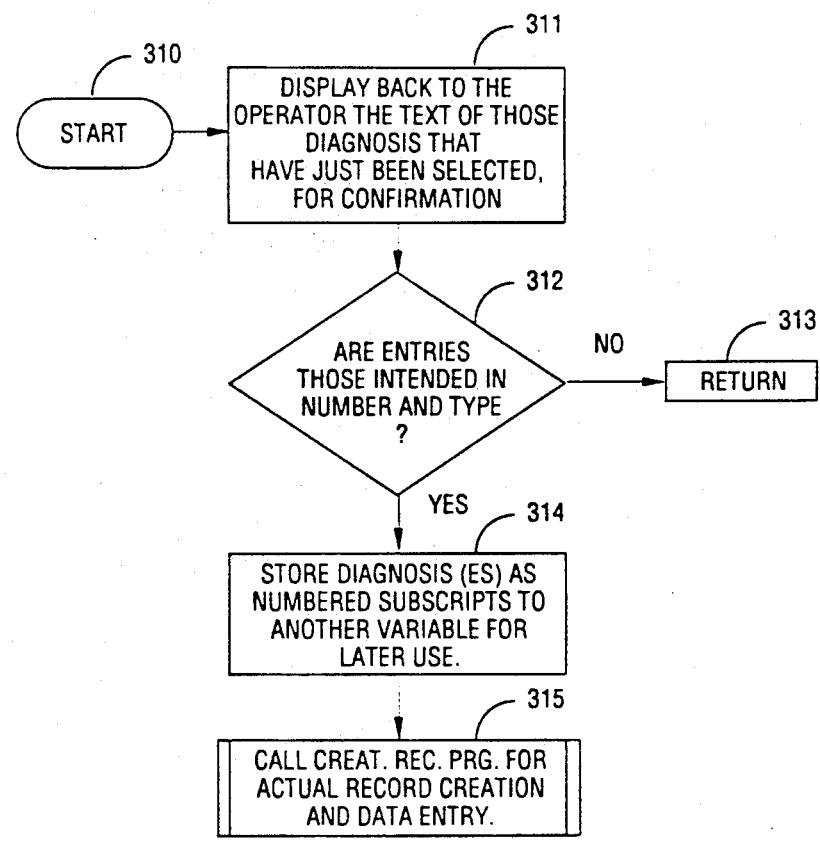
FIG. #3

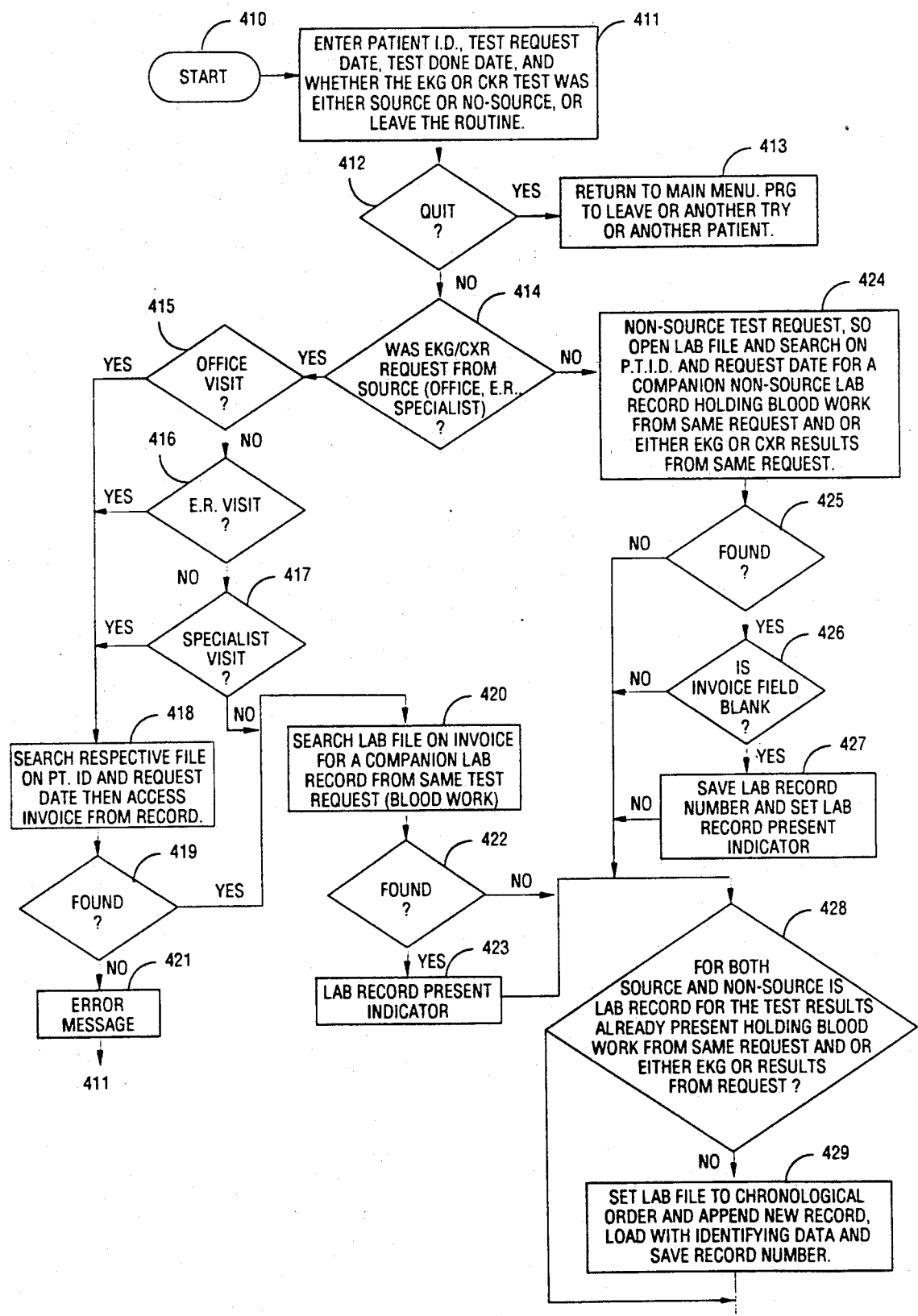
FIG. # 4

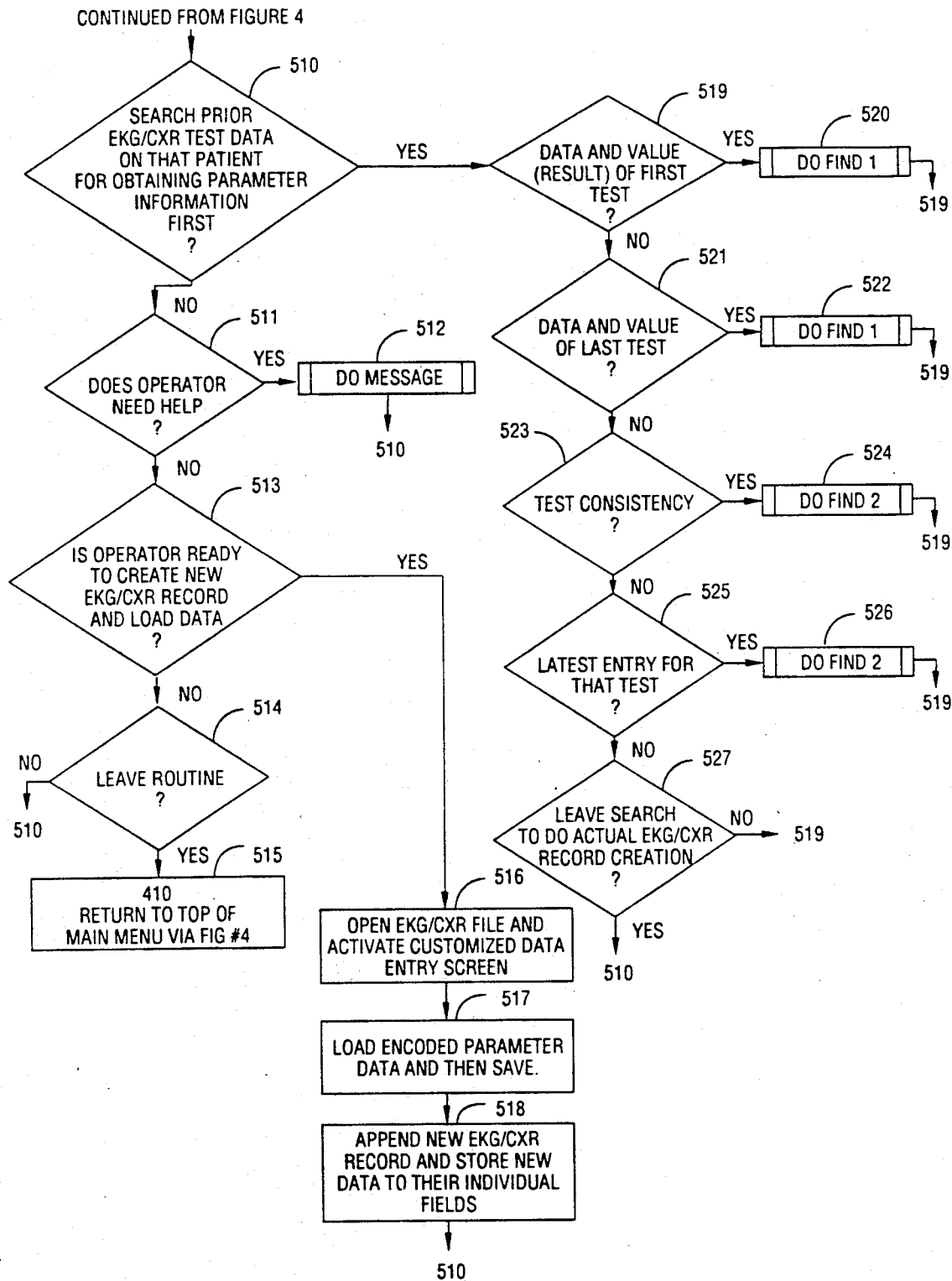
FIG. #5

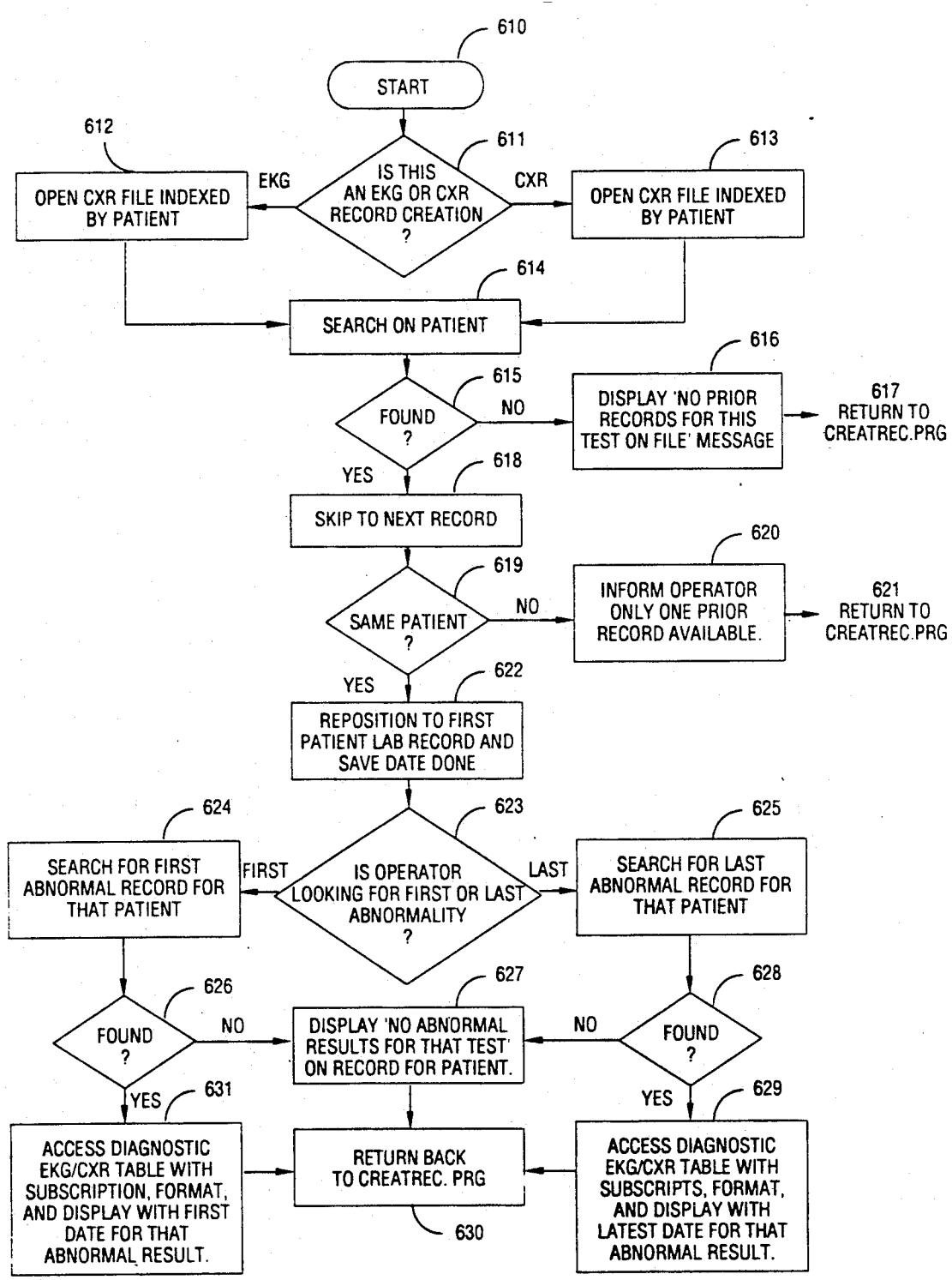
FIG. #6

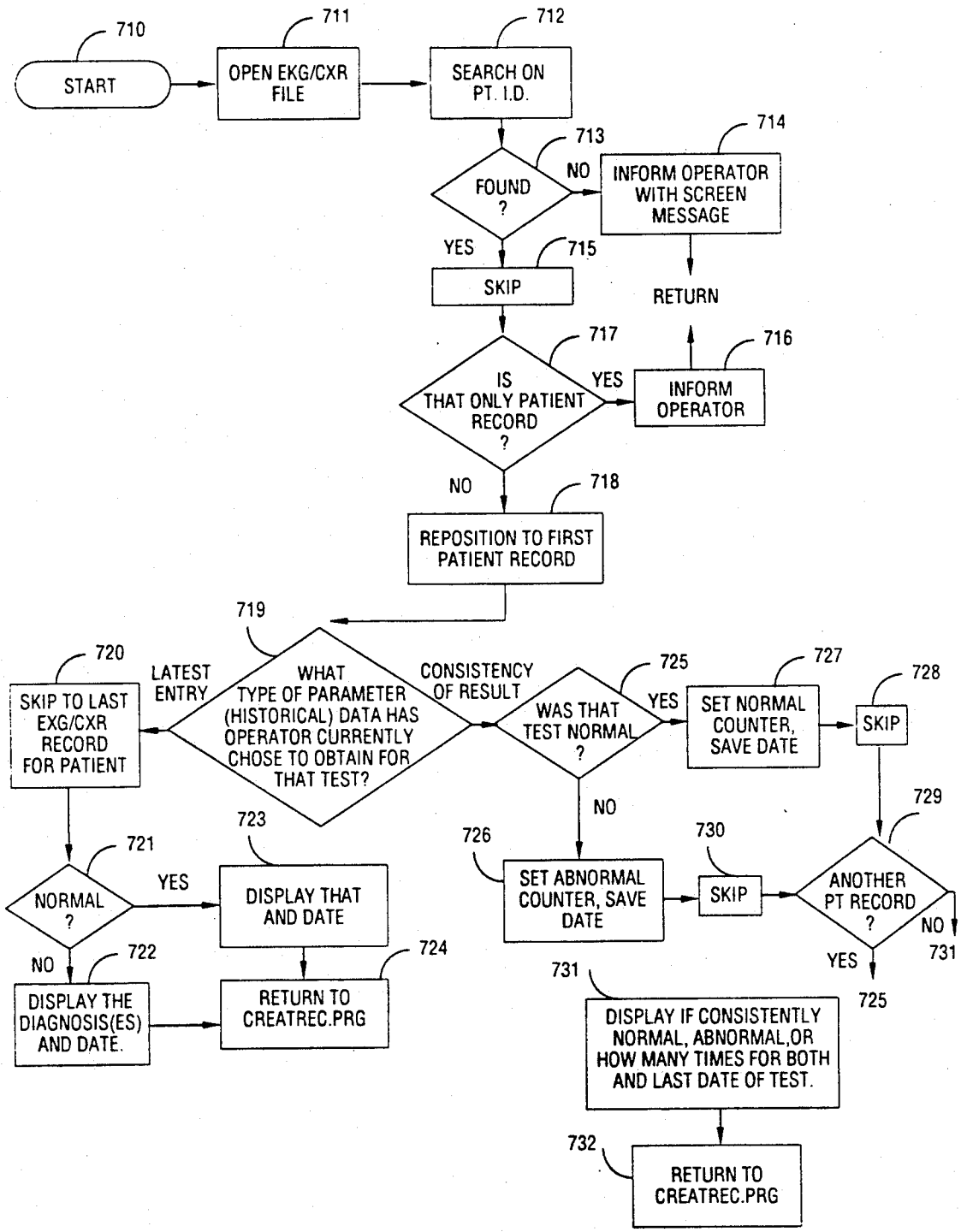
FIG. # 7

PROTOTYPE SOURCE DOCUMENT FOR EKG/CXR DATA ENTRY

| 810 PATIENT I.D. | 811 REQUEST DATE | 812 DONE DATE | 813 SOURCE OF TEST | 814 EKG/CXR DIAGNOSIS (MAX OF 4) |
|---|---|---|---|---|
| ___ ___/___ ___/___ ___ ___ ___ | ___ ___/___ ___/___ ___ | ___ ___/___ ___/___ ___ | O = Office<br>E = Emergency<br>S = Specialist<br>N = Non-formal<br>    (telephone) | chr. inf. wall infarct<br>probable pulm. edema |

FORMAL

FIG. # 8

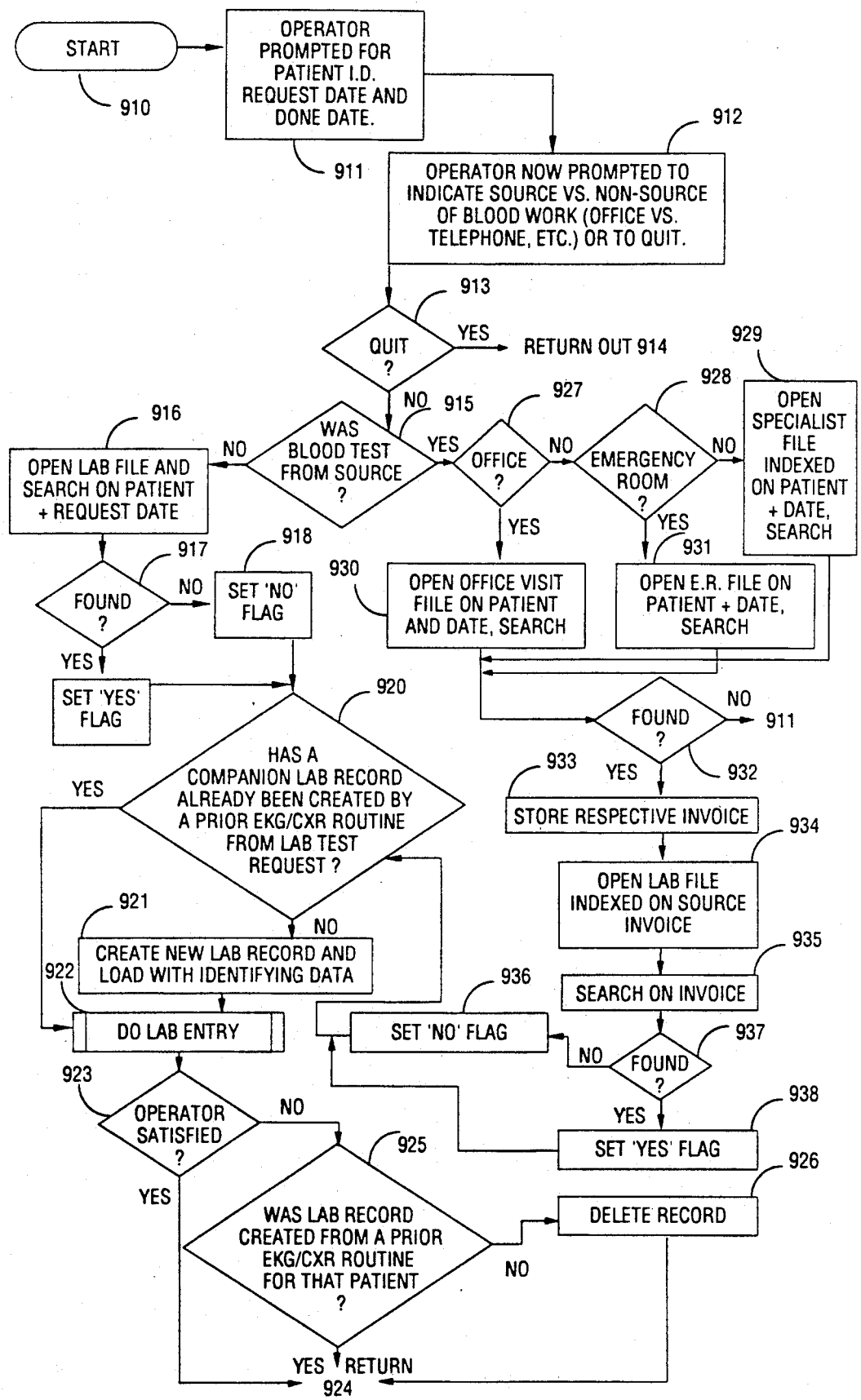
FIG. # 9

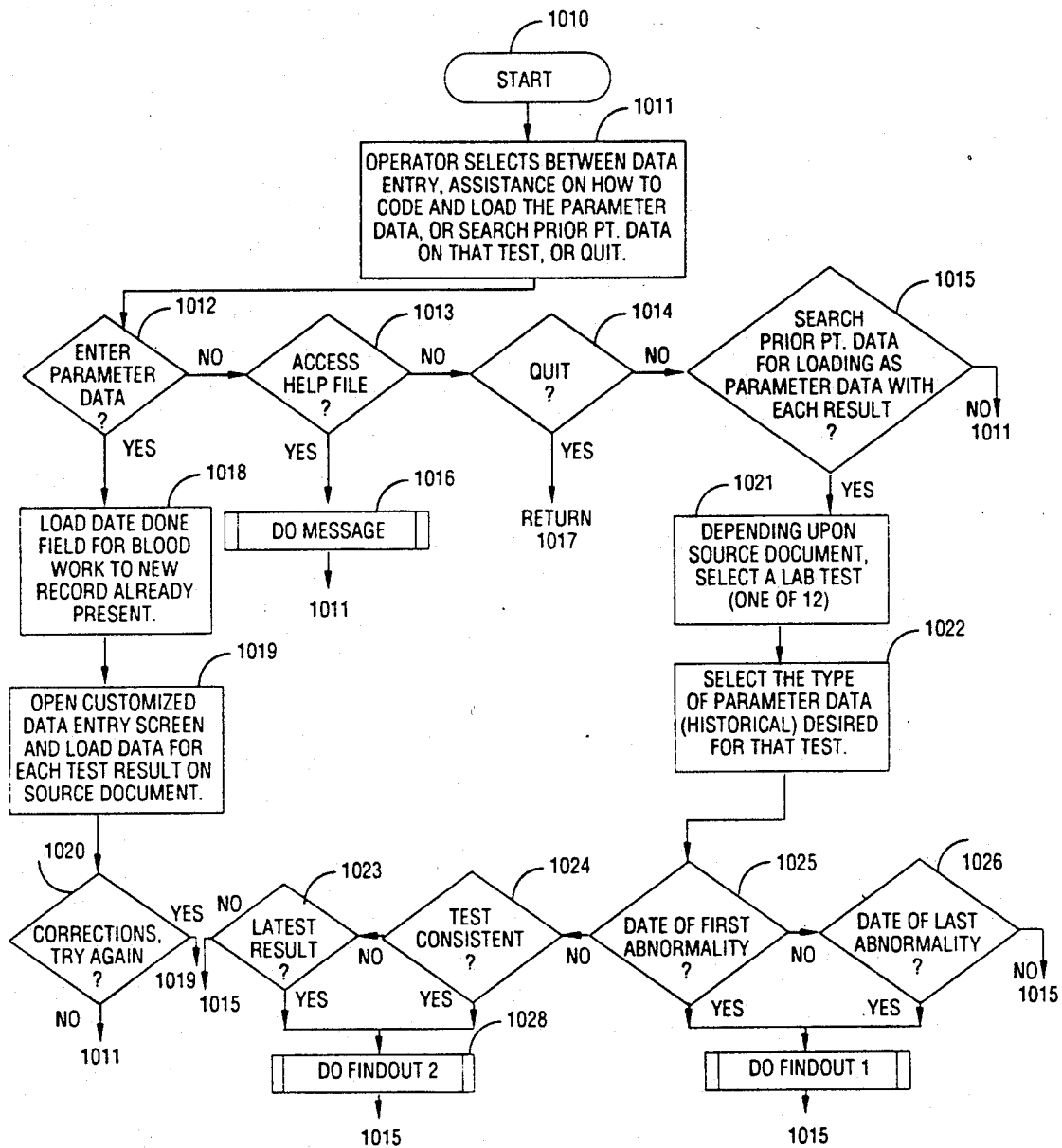
FIG. # 10

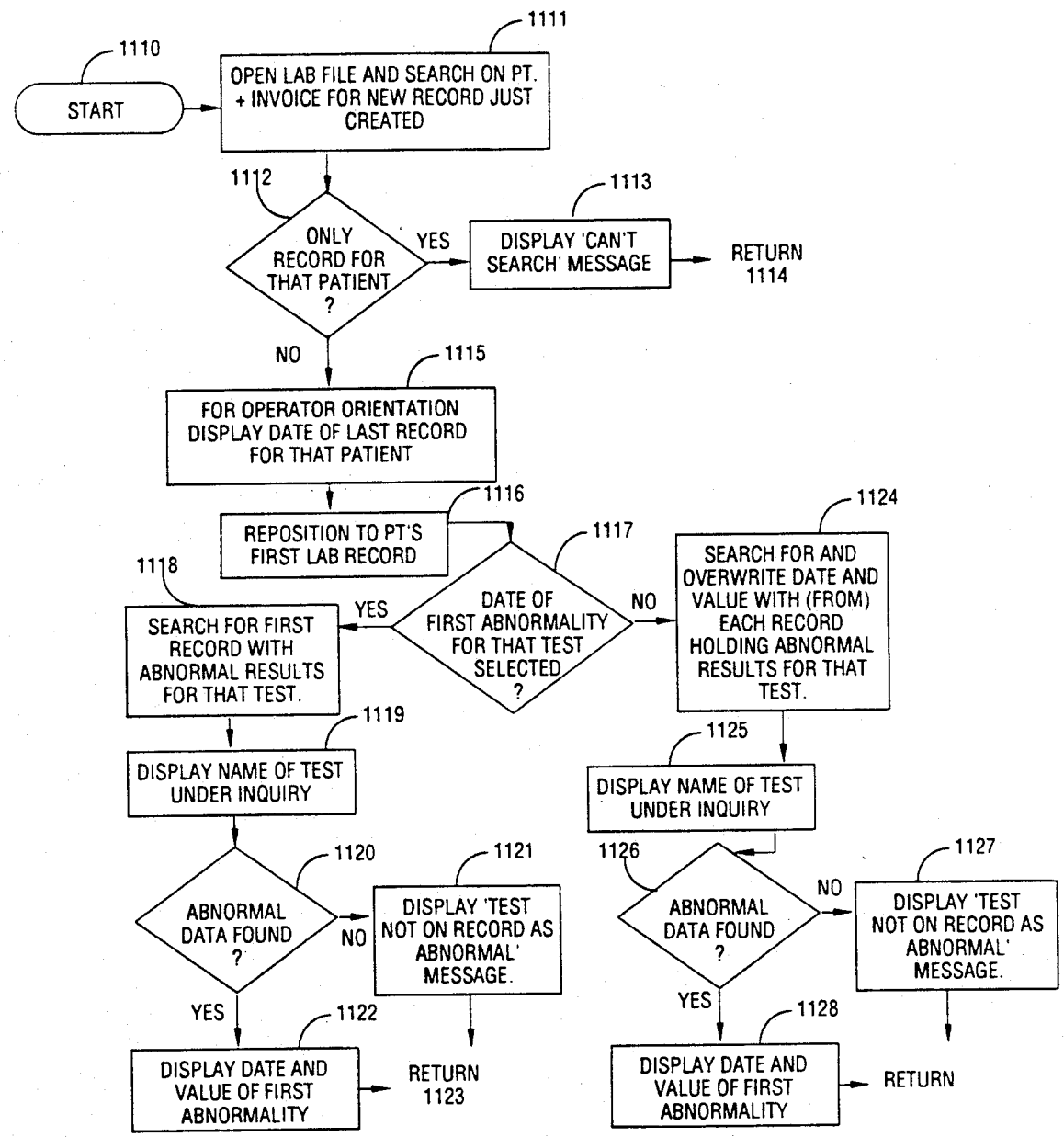
FIG. #11

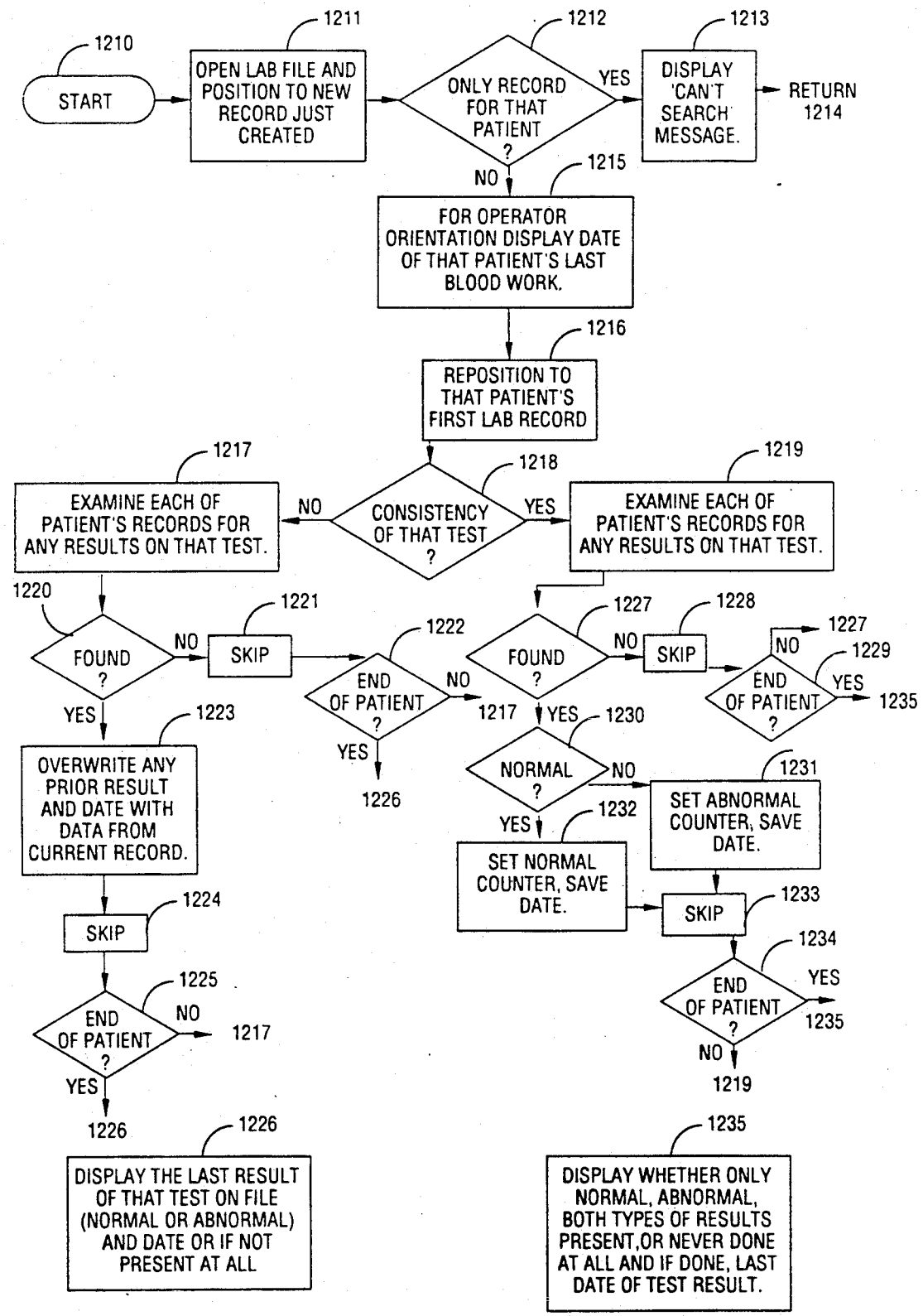
FIG. # 12

| 1310 | 1311 | 1312 | 1313 | 1314 |
|---|---|---|---|---|
| PATIENT I.D. | REQUEST DATE | DONE DATE | SOURCE OF ORIGIN | BLOOD TEST REQUEST (EX) |
| __ __ /__ /__ __ | __ __ /__ /__ __ | __ __ /__ /__ __ | O = OFFICE VISIT<br>E = EMERGENCY ROOM<br>S = SPECIALIST<br>N = NON-SOURCE (INFORMAL) | BUN - - - -<br>CR 10, 6<br>HG – WNL<br>SEDRATE - - - -<br>POTTASIUM – WNL<br>BLD. SUGAR –230<br>PH - - - -<br>PO2 - - - -<br>PO3 - - - -<br>WBC 19.5<br>CALCIUM –5.5 –°<br>HCT 26.4 |

FORMAL

FIG. # 13

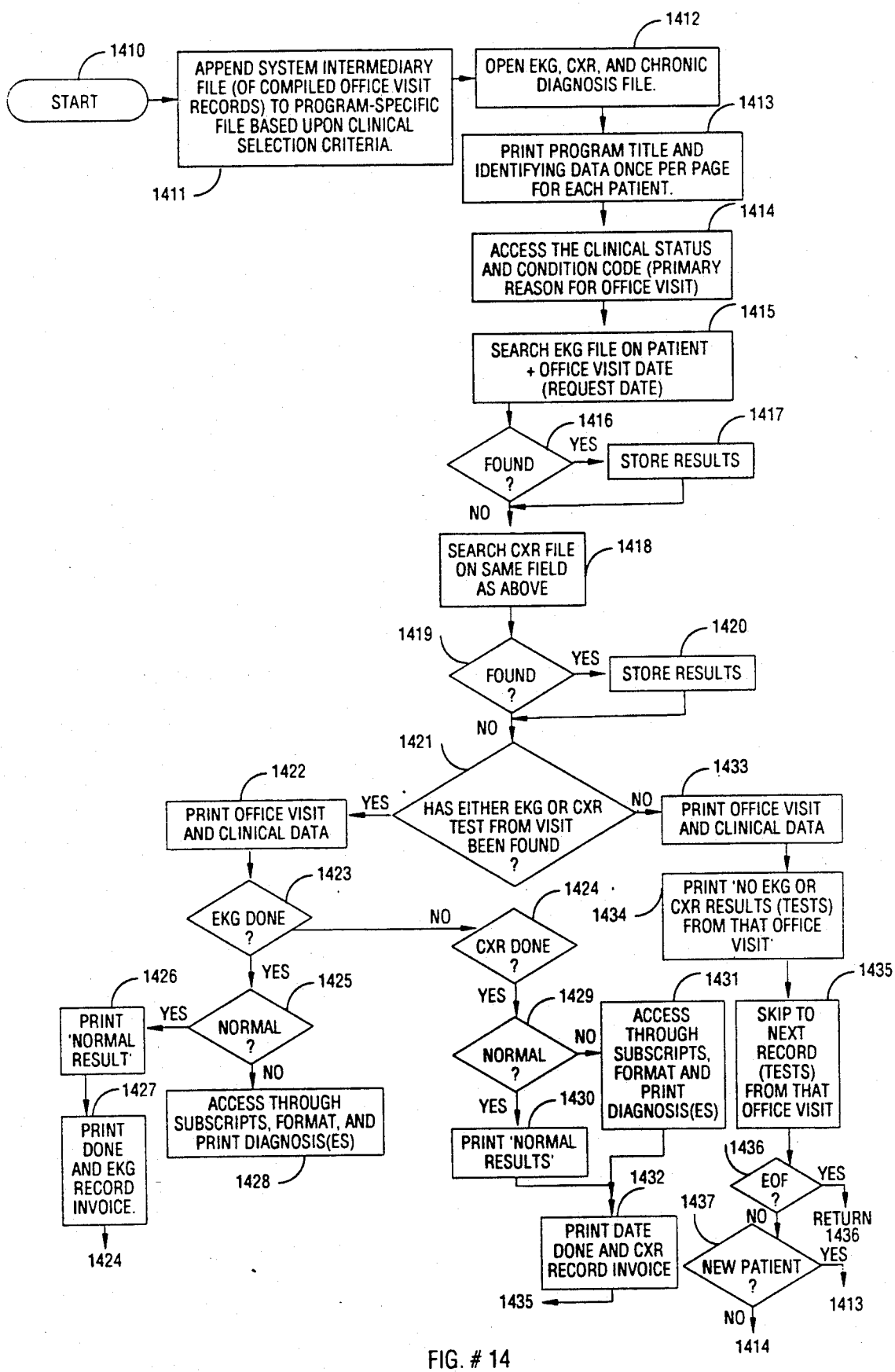
FIG. #14

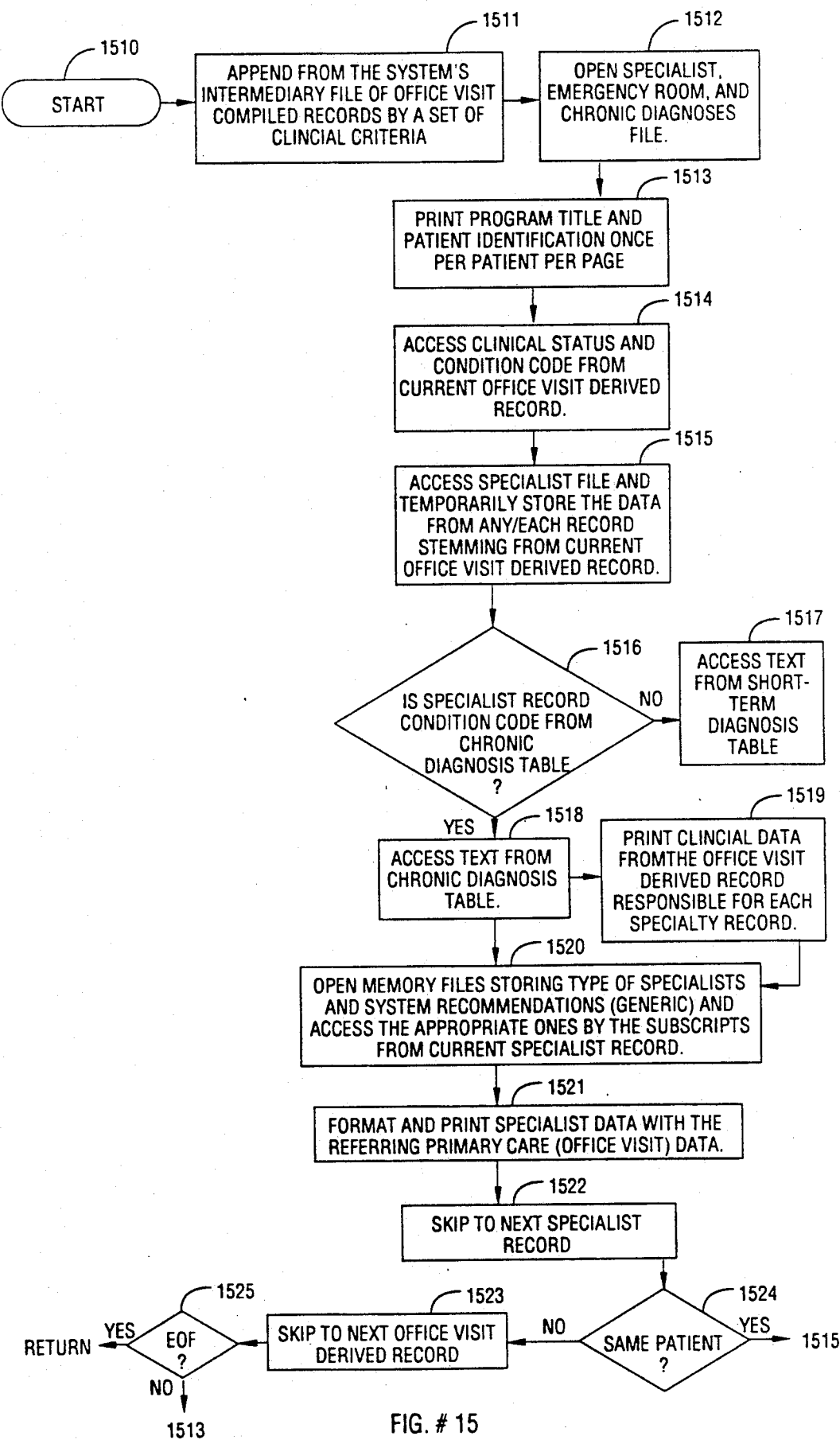
FIG. # 15

FIG #16

CHRONIC PROBLEM ekg and/or cxr data for
unstable cardiac patients(all categories)

PATIENT ID: 013-32-5312 CLINICAL CATEGORY(prim.dx.):B

OFFICE DATE:03/19/87 STATUS:3(sev. sx.) PRIM.OFF.DX:CHF,CHR.VENT.HYPERTROPHY
THE EKG DIAGNOSIS(es) DATE DONE:03/22/87 INVOICE:000000
chr. ant. wall ischemia biventricular hypertropy
acute ant. wall isch.
THE CXR DIAGNOSIS(es) DATE DONE:03/21/87 INVOICE:000000
mod(r)lung infiltrate   bilateral infiltrates
prob.pul edema left vent.hyper OFFICE DATE:03/21/87 STATUS:2(mild sx.) PRIM.OFF.DX:CHF,CHR.VENT.HYPERTROPHY
THE EKG DIAGNOSIS(es) DATE DONE:03/23/87 INVOICE:000011
shortened pr interval   chr. inf. wall ischemia
u waves
THE CXR DIAGNOSIS(es) DATE DONE:03/22/87 INVOICE:000011
mod(r)lung infiltrate

FIG #17

```
CHRONIC PROBLEM ekg and/or cxr data for
     unstable cardiac patients(all categories)

PATIENT ID:112-23-3145 CLINICAL CATEGORY(prim.dx.):b

OFFICE DATE:03/25/87 STATUS:2(mild sx.) PRIM.OFF.DX:CHRONIC ANGINA
THE CXR DIAGNOSIS(es) DATE DONE:03/26/87 INVOICE:000007
mod(r)lung infiltrate    mod(l)lung infiltrate OFFICE DATE:03/28/87 STATUS:5(hospital) PRIM.OFF.DX:CHRONIC ANGINA
THE EKG DIAGNOSIS(es) DATE DONE:03/29/87      INVOICE:000014
shortened pr interval    chr. ant. wall ischemia
chr. inf. wall ischemia
THE CXR DIAGNOSIS(es) DATE DONE:03/29/87 INVOICE:000014
mod(l)lung infiltrate     ext.infiltrates(r)
single lesion(l)
```

FIG #18

CHRONIC PROBLEM ekg and/or cxr data for
unstable cardiac patients(all categories)

PATIENT ID:114-24-3145 CLINICAL CATEGORY(prim.dx.):A

OFFICE DATE:03/27/87 STATUS:5(hospital) PRIM.OFF.DX:ACUTE ANGINA,UNSTABLE
EKG:WITHIN NORMAL LIMITS DATE DONE:03/28/87 INVOICE:000002
THE CXR DIAGNOSIS(es) DATE DONE:03/29/87 INVOICE:000002
prob.pul edema    left vent.hyper

FIG #19

CHRONIC PROBLEM ekg and/or cxr data for
unstable cardiac patients(all categories)

PATIENT ID:131-25-6721 CLINICAL CATEGORY(prim.dx.):A

OFFICE DATE:03/20/87 STATUS:4(imprvmnt) PRIM.OFF.DX:ACUTE ANGINA,UNSTABLE,CHF
THE EKG DIAGNOSIS(es) DATE DONE:03/21/87 INVOICE:000012
prolonged pr interval    chr. ant. wall ischemia
chr.lat.wall ischemia    chr. inf. wall ischemia
THE CXR DIAGNOSIS(es) DATE DONE:03/22/87    INVOICE:000012
mod(r)lung infiltrate    ext.infiltrates(r+l)

OFFICE DATE:03/27/87 STATUS:2(mild sx.) PRIM.OFF.DX:ACUTE ANGINA,UNSTABLE,CHF
THE EKG DIAGNOSIS(es) DATE DONE:03/29/87 INVOICE:000027
shortened pr interval    chr.lat.wall ischemia
biventricular hypertropy
THE CXR DIAGNOSIS(es)      DATE DONE:03/27/87 INVOICE:000027
mod(r)lung infiltrate    bilateral infiltrates
prob.pul edema

FIG #20

CHRONIC PROBLEM ekg and/or cxr data for
unstable cardiac patients(all categories)
=========================================
=========================================
PATIENT ID:152-43-2916 CLINICAL CATEGORY(prim.dx.):B
=========================================
=========================================
no ekg or cxr data available from that visit
office date:03/22/87 INVOICE:000016 status:4(imprvmnt) prim.off.dx.:CHRONIC ANGINA

```
CHRONIC PROBLEM ekg and/or cxr data for
     unstable cardiac patients(all categories)
=================================================================
-----------------------------------------------------------------
PATIENT ID:212-32-5487 CLINICAL CATEGORY(prim.dx.):A
-----------------------------------------------------------------
OFFICE DATE:03/19/87 STATUS:3(sev. sx.) PRIM.OFF.DX:ACUTE ANGINA,UNSTABLE
THE EKG DIAGNOSIS(es) DATE DONE:03/20/87 INVOICE:000029
shortened pr interval      chr. ant. wall ischemia
u·waves
THE CXR DIAGNOSIS(es) DATE DONE:03/21/87        INVOICE:000029
mod(r)lung infiltrate      mod(l)lung infiltrate
prob.pul edema             bilat. cardiomegaly
-----------------------------------------------------------------
OFFICE DATE:03/26/87 STATUS:4(imprvmnt) PRIM.OFF.DX:ACUTE ANGINA,UNSTABLE
THE EKG DIAGNOSIS(es) DATE DONE:03/26/87 INVOICE:000032
shortened pr interval      chr.lat.wall ischemia
acute ant. wall isch.
CXR:WITHIN NORMAL LIMITSDATEDONE:03/27/87 INVOICE:000032
-----------------------------------------------------------------
```

```
CHRONIC PROBLEM ekg and/or cxr data for
unstable cardiac patients(all categories)

PATIENT ID:324-53-0764 CLINICAL CATEGORY(prim.dx.):A

OFFICE DATE:03/19/87 STATUS:3(sev. sx.) PRIM.OFF.DX:ACUTE ANGINA,UNSTABLE
THE EKG DIAGNOSIS(es) DATE DONE:03/20/87 INVOICE:000036
flattened t waves
acute ant. wall isch.
THE CXR DIAGNOSIS(es)      DATE DONE:03/22/87 INVOICE:000036
mod(1)lung infiltrate        ext.infiltrates(r)

OFFICE DATE:03/21/87 STATUS:5(hospital) PRIM.OFF.DX:ACUTE ANGINA,UNSTABLE
THE EKG DIAGNOSIS(es) DATE DONE:03/22/87 INVOICE:000041
prolonged pr interval        biventricular hypertropy
acute ant. wall isch.
```

FIG #23

```
CHRONIC PROBLEM specialty(referral) data for
     unstable cardiac patients(all categories)

PATIENT ID:031-32-5312 CLINICAL CATEGORY(prim.dx.):B original primary care off. date:03/19/87
STATUS:3(sev. sx.) PRIM.off.dx:CHF,CHR.VENT.HYPERTROPHY
cardiologist office date:03/22/87 INVOICE:S00003
cardiologist recommendations                    return date:03/29/87
med addition         change existing meds
condition stable
cardiologist dx:early chf original primary care off. date:03/19/87
STATUS:3(sev. sx) PRIM.off.dx:CHF,CHR.VENT.HYPERTROPHY
cardiologist office date:03/29/87 INVOICE:S00010
cardiologist recommendations
continue with present rx      diet/opc rx
more lab tests                med addition
condition stable
cardiologist dx:CHF,CHR.VENT.HYPERTROPHY   no re-evaluation indicated DATA ERROR, office visit from date:03/21/87 invoice:000011
has consult indicated, but no matching specialist record found
```

FIG #24

CHRONIC PROBLEM specialty(referral) data for
unstable cardiac patients(all categories)

PATIENT ID:013-32-6721 CLINICAL CATEGORY(prim.dx.):B original primary care off. date:03/09/87
STATUS:2(mild sx.) PRIM.off.dx:CHF,CHR.VENT.HYPERTROPHY
cardiologist office date:03/09/87 INVOICE:S00000
cardiologist recommendations    diet/opc rx
med deletions                   more lab tests
condition stable
cardiologist dx:ACUTE ANGINA,UNSTABLE,CHF no re-evaluation indicated

FIG #25

CHRONIC PROBLEM specialty(referral) data for
unstable cardiac patients(all categories)

PATIENT ID:112-23-3145 CLINCIAL CATEGORY(prim.dx.):B original primary care off. date:03/25/87
STATUS:2(mild sx.) PRIM.off.dx:CHRONIC ANGINA
cardiologist office date:03/27/87 INVOICE:S00009
cardiologist recommendations
continue with presnt rx          med addition
condition stable
cardiologist dx:CHRONIC ANGINA           no re-evaluation indicated DATA ERROR,office visit from date:03/28/87 invoice:000014
has consult indicated, but no matching specialist record found

FIG #26

```
CHRONIC PROBLEM specialty(referral) data for
     unstable cardiac patients(all categories)

PATIENT ID:114-24-3145 CLINICAL CATEGORY(prim.dx.):A original primary care off. date:03/27/87
STATUS:5(hospital) PRIM.off.dx:ACUTE ANGINA,UNSTABLE
cardiologist office dte:03/28/87 INVOICE:S00009
cardiologist recommendations
med addition           change existing meds
diet/opc rx            condition stable
hospitalization        more lab tests
surg. is indicated
cardiologist dx:early chf           return date:04/02/87 original primary care off. date:03/27/87
STATUS:5(hospital) PRIM.off.dx:ACUTE ANGINA,UNSTABLE
cardiologist office date:04/02/87 INVOICE:S00013
cardiologist recommendations
med addition           change existing meds
cardiologist dx:early chf           return date:04/13/87 original primary care off. date:03/27/87
STATUS:5(hospital) PRIM.off.dx:ACUTE ANGINA,UNSTABLE
cardiologist office date:04/13/87 INVOICE:S00016
cardiologist recommendations
continue with present rx    condition stable
cardiologist dx:ACUTE ANGINA,UNSTABLE   no re-evaluation indicated
```

FIG #27

```
CHRONIC PROBLEM specialty(referral) data for
    unstable cardiac patients(all categories)

PATIENT ID:131-25-6721 CLINICAL CATEGORY(prim.dx.):A original primary care off. date:03/09/87
STATUS:4(imprvmnt) PRIM.off.dx:ACUTE ANGINA,UNSTABLE,CHF
cardiologist office date:03/12/87 INVOICE:S00007
cardiologist recommendations
med addition            med deletions
diet/opc rx
cardiologist dx:ACUTE ANGINA,UNSTABLE,CHF no re-evaluation indicated original primary care off. date:03/27/87
STATUS:2(mild sx.) PRIM.off.dx:ACUTE ANGINA,UNSTABLE,CHF
gastroenterologist office date:03/29/87 INVOICE:S00007
gastroenterologist recommendations
med addition            med deletions
diet/opc rx             condition stable
gastroenterologist dx:gastritis,mild    no re-evaluation indicated
```

FIG #28

CHRONIC PROBLEM specialty(referral) data for
unstable cardiac patients(all categories)

PATIENT ID:152-43-2916 CLINICAL CATEGORY(prim.dx.):B original primary care off. date:03/22/87
STATUS:4(imprvmnt) PRIM.off.dx:CHRONIC ANGINA
cardiologist office date:03/25/87 INVOICE:S00011
cardiologist recommendations       med addition
continue with present rx
condition stable
cardiologist dx:CHRONIC ANGINA            no re-evaluation indicated

FIG #29

```
CHRONIC PROBLEM specialty(referral) data for
    unstable cardiac patients(all categories)

PATIENT ID:212-32-5487 CLINICAL CATEGORY(prim.dx.):A
STATUS:3(sev. sx.) PRIM.off.dx:ACUTE ANGINA,UNSTABLE
original primary care off. date:03/19/87
cardiologist office date:03/22/87 INVOICE:S00014
cardiologist recommendations
continue with present rx    diet/opc rx
cardiologist dx:ACUTE ANGINA,UNSTABLE   no -re-evaluation indicated
```

FIG #30

CHRONIC PROBLEM specialty(referral) data for
unstable cardiac patients(all categories)

PATIENT ID:324-53-0764   CLINICAL CATEGORY(prim.dx.):A original primary care off. date:03/19/87
STATUS:3(sev. sx.)  PRIM.off.dx:ACUTE ANGINA,UNSTABLE
cardiologist office date:03/22/87 INVOICE:S00020
cardiologist recommendations      more lab tests
med addition
cardiologist dx:angina,no ischemia    return date:03/27/89 original primary care off. date:03/19/87
STATUS:3(sev. sx.)  PRIM.off.dx:ACUTE ANGINA,UNSTABLE
cardiologist office date:03/29/87 INVOICE:S00026
cardiologist recommendations
continue with present rx     condition stable
more lab tests
cardiologist dx:ACUTE ANGINA,UNSTABLE        no re-evaluation indicated original primary care off. date:04/06/87
STATUS:5(hospital) PRIM.off.dx:ACUTE ANGINA,UNSTABLE
hematologist office date:04/09/87 INVOICE:S00034
hematologist recommendations
continue with present rx     condition stable
hematologist dx:CHR.PANCREATITIES        no re-evaluation indicated

MODEL USER APPLICATION SYSTEM FOR CLINICAL DATA PROCESSING THAT TRACKS AND MONITORS A SIMULATED OUT-PATIENT MEDICAL PRACTICE USING DATA BASE MANAGEMENT SOFTWARE

BACKGROUND OF THE INVENTION

The following work builds upon the subject matter disclosed in an earlier filed U.S. application, Ser. No. 07/542,752, currently pending, which is incorporated herein by reference. That earlier and more comprehensive work was based upon a scheme of hierarchical diagnostic classification for patient ranking and data processing. It generally dealt with a computer-based tracking and monitoring system for the retrospective analysis of patient care results, physician performance and clinical resource management in a primary care out-patient environment. In this earlier work, specific programs were designed to mimic common aspects of out-patient clinical medicine, and specifically allowed for the detection and compilation of unjustified (overuse) office visits, both scheduled and unscheduled, according to a set of computer program specified criterion, the tracking the nature of patient care during protracted episodes of out-patient illnesses at varying levels of clinical severity, the identifying of unnecessary lab work during unremarkable office visits, the monitoring of impending or actual medication induced toxicity, the medication and physical data on cardiac patients during serious symptoms, etc.

In the prior work, the bulk of the pool of clinical data which was used in processing originated from the primary care out-patient visit, both scheduled and unscheduled. Such data included treatment modalities (medication), physical data observation (signs and symptoms), diagnostic tests, etc. All of these were encoded and stored logically in different, related files. Each patient's files were linked by common data fields. These records were created and loaded through prototype data entry routines.

The earlier work, however, did not address some common problems which occur in this environment. First, there is frequently disparity in time (days) between the running of two different types of tests which originate from the same lab test request, such as blood work and EKG/CXR tests. Second, lab tests are sometimes ordered in the absence of or aside from a formal encounter (or "source") office visit. The most frequent example is over the telephone from a spontaneous call by a patient (which is termed a "non-source" request). When this happens there is naturally no link between a source invoice that would normally link various lab tests together. Both problems are not mutually exclusive and are met by the present invention. Further, this invention includes a revision of the specialist record for storing more comprehensive data.

SUMMARY OF THE INVENTION

The present invention consists of a new data entry routine for loading EKG and CXR test results into separate EKG/CXR records as distinct logical entities. The labor record structure has been revised to allow for linking of separate EKG/CXR data from the same lab request. The lab entry process is now restricted to the entry of blood work only. The specialty record has been improved to contain separate fields for holding data that identifies both the specific type of specialist (cardiologist, neurologist, etc.) and the general recommendation made from a set common to all specialists. A first report generation program combines salient clinical data from office visits with the EKG/CXR tests results ordered during those visits. A second report generation program combines salient clinical data from office visits with the results from the specialist (consultant) visits referred by those (primary care) office visits.

To be more specific, the patient electrocardiographic (EKG) and chest x-ray (CXR) data, loaded through the same program, are now distinct logical entities stored separately and related to other patient data. Consisting of a full complement of standard specialty diagnoses, the EKG/CXR data, as additional medical attributes, adds critical data elements to the system's knowledge base and enhances the ability to clinically profile each patient. For example, a patient's cardiac symptom (or sign) can now be viewed together with EKG results or a pulmonary symptom can be viewed with CXR data from the same office visit. For the purpose of population analysis, information can be obtained regarding the frequency of EKG abnormalities in patients with certain diagnosis and/or taking certain medication within a certain age range amongst pre-selected doctors.

The lab record data routine is now limited to blood work only (such as bun, Hct, wbc, etc.). However, each time the EKG/CXR data entry routine is run, historical parameter data from the EKG/CXR results are passed to a "companion" lab record along with other data linking both record types. If a labor record isn't already present storing blood work results from the same lab test request, a lab record will be created using the EKG/CXR data entry routine. Similarly, if a lab test request contains orders for both EKG or CXR and blood work, and the EKG or CXR (or both) tests were done first and therefore entered first, a lab record will already be present when the lab data entry routine is run at a latter time. Upon completion of the lab data (blood work) entry routine, the request date will hold the value common to both types of tests (EKG and blood work), the date done field will indicate when the blood work was done and the invoice field of both EKG/CXR and lab record indicating origin will be identical. Such cross-file processing from EKG/CXR to the lab record ensures that the lab record will, in the case of both test types from the same lab test request, hold all the results of lab work taken at that time for that patient. If on the other hand, only EKG/CXR tests were done, a lab record will still be created from the EKG/CXR parameter data. As such, one single composite record may be accessed to review all the lab test results for any patient taken at any time for many general purposes, while at the same time, more explicit and definitive information of a current and fuller nature regarding the EKG/CXR data from the same lab test request is held separately in linked files.

Within the above design for both EKG/CXR and lab data entry, a provision has been made for including and identifying lab test results (EKG/CXR, blood work) ordered in the absence of a formal patient-physician encounter (called a "non-source" encounter). These non-source encounters include tests ordered over the phone or in some other informal way. Those records will be properly identified and matched in cases where both types of tests (CXR and EKG) have been ordered by a blank invoice field and a specific request date. Since that type of practice occurs frequently enough, any information management system that fails to take it into account can lack significant patient data.

The specialty record improvements consist of the addition of separate fields for holding data that identifies both the specific type of specialist (cardiologist, neurologist, etc.) and the general recommendations made from a set common to all. Also, a field has been added to include a request data which is especially important for tracking successive visits to the same specialist stemming from a single original office visit (primary care) referral.

One print program consists of printing out EKG and CXR test results in association with other clinical data documented during the same office visit in which those tests were ordered. Another print program prints out specialty data, such as type of specialist and recommendations, in association with other clinical data documented during those office visits in which the specialty referrals were made.

BRIEF DESCRIPTION OF THE DRAWINGS

FIG. 1 illustrates the principal steps in the main calling program (mainmenu.prg). The main calling program contains both the initial and final segments of the EKG/CXR data entry routine.

FIG. 2 illustrates the principal steps in the program (menu.prg) that generates a list of diagnostic choices for display.

FIG. 3 illustrates the principal steps of the program (menu.prg) which allows the operator to confirm the test result entries and then either pass control back to FIG. 1 or the next sequential segment of the routine illustrated by FIG. 4.

FIG. 4 illustrates the principal steps in the program (creatrec.prg) for ascertaining the source of the test request, for accessing appropriate record identifying data and for locating or creating the companion (master) lab record.

FIG. 5 continues from FIG. 4. This segment illustrates the program for enabling the operator to select the kind of historical data to accompany the current EKG/CXR test results. This segment also involves the actual creation and loading of the new EKG/CXR records.

FIG. 6 illustrates the principal steps in a subroutine (find1.prg) for determining and displaying to the operator two (of four possible) types of any prior results of that patient's EKG/CXR test, which are then used to compile the parameter data into encoded form.

FIG. 7 illustrates the principal steps in a subroutine (find2.prg) for determining and displaying to the operator two other types of any prior results of that patient's EKG/CXR test.

FIG. 8 illustrates a prototype source document prepared by the medical department for used in the data entry routine for either EKG or CXR test results.

FIG. 9 illustrates the principal steps in the main calling program (labfirst.prg) for ascertaining the source of the text request, and creating, if necessary, the new lab record and for loading the lab record with identifying data prior to actual entry of the test results.

FIG. 10 illustrates the principal steps of a program (labentry.prg) for obtaining prior results of blood work tests, and for the actual entry of current data to the lab record.

FIG. 11 illustrates the principal steps of a program (findout1.prg) for determining and displaying to the operator two types of (of four possible) of prior results pertaining to the particular blood work test results to be entered.

FIG. 12 illustrates the principal steps of a program (findout2.prg) for determining and displaying to the operator the two other types of prior results pertaining to the particular blood work test results to be entered.

FIG. 13 illustrates a prototype source document prepared by the medical department for the lab record (blood work) data entry routine.

FIG. 14 illustrates the principal steps of a report generation program (print6.prg) that combines salient clinical data from office visits with the EKG/CXR test results ordered during those visits.

FIG. 15 illustrates the principal steps of a report generation program (print7.prg) for combining salient clinical data from office visits with the results from the specialist (consultant) visits referred by those (primary care) office visits.

FIGS. 16–22 show reports generated by the program print6.prg in which salient clinical data from preselected office visits are combined with the EKG or CXR (or both) test results ordered during those visits. Note the possible disparity in time between the two types of tests in cases where both were ordered from the same visit.

FIGS. 23–30 show reports generated by the program print7.prg in which salient clinical data from preselected office visits are combined with the specialty results from referrals made during those office visits. Note that in some cases (FIGS. 23, 26 and 30) more than one specialty referral was made from the same office visit. Also note that the type of specialist in each case is made explicit and the recommendations are generic in nature for common use with all specialists.

DESCRIPTION OF PREFERRED EMBODIMENTS

1. EKG (electrocardiographic) and/or CXR (chest x-ray) record creation and data entry routine.

FIG. 1 illustrates the principal steps in the main program (mainmenu.prg) for creating both EKG and CXR records. This program is entered separately for each record creation, EKG or CXR, even if both records are for the same patient. It begins in step (111) by allowing the operator to choose between EKG or CXR for any patient. Then, depending upon the choice, the program will generate a corresponding screen display listing fourteen standard, commonly used technical abnormalities (including just "normal") in step (117). The operator chooses the abnormality which matches that given on the operator's source document previously prepared by the medical department for use in transcription by the data entry department (a prototype of that source document is shown in FIG. 8).

The actual selections are made by allowing the operator to move up and down through the list of fourteen diagnostic options until the appropriate matches are found between the screen display and that present on the source document, up to a maximum of four selections. In order to enter a diagnosis the return key must be pressed while the cursor is positioned to that selection. Immediately and automatically after the diagnostic selections are made, the program will echo back only those diagnoses selected for cross-checking and confirmation in step (120). If a mistake has been made or an error in the number of selections has been made, the program returns to the entry screen for re-entry of data. Instructions are present on both EKG and CXR screen for assisting the operator in the proper method and steps for selecting each diagnosis. The diagnoses are handled as subscripts corresponding to individual table entries, as discussed later. FIGS. 2 and 3 to give a more detailed description of the procedure for entering diagnoses.

When the operator is satisfied that the appropriate selections have been made, the program (mainmenu.prg) then "carries" those EKG or CXR diagnoses into the segment (creatrec. prg) in the form of subscripts. FIGS. 4 and 5 illustrate the principal steps in the creatrec.prg. In step (411) basic identifying data, such as patient I.D., date of request, data test completed, is solicited. In step (414) the operator is then asked to indicate the nature of the encounter existent at the time the "lab test request" was made —either "source" (which includes office visit, emergency room (E.R.) or specialist) or "non-source" (which includes hallway or telephone). A complete "lab test request" consists of both EKG/CXR and a battery of fourteen blood tests which for the purpose of this application will include at least EKG or CXR with or without associated blood work. In the case "source" encounter is specified, the operator is requested to select either office visit, E.R. or specialist, depending on the nature of the encounter in steps (415), (416) and (417). This information is used to access the record's invoice number which is to be also used in cross-linking the three records which will then be related a a result of this segment (creatrec.prg): the source record already present, the EKG or CXR record to be created, and the related lab record which may or may not already exist depending upon the co-existence of other tests also ordered and already done, originating from the same encounter (source or non-source). If a non-source (hallway or telephone) is indicated in step (414), then the creatrec.prg segment just searches the laboratory file to determine if a record already exists holding other test results ordered at the same time. In both cases, source or non-source, where a "companion" lab record is not already present, one will be created prior to the EKG or CXR record creation and data entry step and loaded with identifying data for eventual cross-linkage (such as request date and, if source, invoice number).

Upon finding or creating the related lab record (in both source and non-source encounter) the appropriate parameter data is then obtained by the operator through called subprograms, which are activated by menu selections. The subprograms (find1.prg and find2.prg) access and display a variety of previous EKG (or CXR) data for that patient, such as date of first abnormality, most recent results, etc. The principal steps in these subprograms are illustrated in FIGS. 6 and 7. A customized data entry screen is then generated (format file) for the operator to directly enter three parameter codes (based upon information previously obtained). The entry screen also displays the original identifying data, including patient I.D., request data and date test done, for operator confirmation. Then a blank record is created and appended to either the EKG or CXR file (depending upon which test result is being loaded) and all of the above data (present in the custom data entry screen) is written to that blank record including the subscripts collected earlier representing the diagnoses. In cases where the EKG or CXR test was normal the record will contain only two characters of data, one indicating "normality" and the other for indicating most recent result (if present). The parameter data is then written to the cross-linked "companion" lab record (which may also contain other test results). Thus, an EKG and/or CXR record is created and cross-linked to other related system files for that patient: lab record and in the vast majority of cases, the "source" record.

2. Laboratory (blood work) data entry routine (labfirst.prg, labentry.prg, findout1.prg and findout2.prg).

The current routine has been revised over that disclosed in Ser. no. 07/542,752 in order to adjust for the system's addition of EKG/CXR test result data as complete an separate clinical entities now being stored in their own logically related files. The current routine now takes into account the possibility that the lab record for holding the blood work results to be entered may already exist due to the prior entry of EKG and/or CXR parameter data from test results originating from the same encounter (both source and non-source) and passed to the lab record created (for holding EKG/CXR parameter data) during that separate EKG/CXR data entry routine run at an earlier time (as illustrated previously). In effect, due to this "cross-file" processing present in the EKG/CXR data entry routine for passing partial parameter test results to a "companion" related lab record, the present routine must now take into account the possibility that the blood test results presently being entered may have been ordered, and originated from, the same encounter (source or non-source) in which an EKG and/or CXR test was also ordered. Also, there is the lesser likelihood that the lab record is already existent due to only some of the original blood work ordered being completed earlier, and the routine is now being run to enter the remaining blood test results for that patient which were ordered from the same lab test request as the test results already on file. This latter possibility, although uncommon, may arise whenever a lab test is ordered for up to fourteen separate elements which conceivably may not be run as a complete unit or battery on the same day.

Pursuant to the above, upon entering the labfirst.prg routine, the specific nature of the encounter, whether source or non-source and then which of the three specific sources, is solicited and then collected in step (912) of FIG. 9. In the case of a source encounter, selecting office visit, E.R. or specialty allows the routine to obtain the appropriate invoice for use in searching throught the lab file to determine if a lab record holding lab test results (including EKG/CXR or earlier done blood work) ordered from same encounter is already present. In the case non-source is specified, the lab file is searched directly by using the request date and patient I.D. as the search indices to determine if a lab record holding other lab tests results is already present. If the routine determines that a prior lab record holding test results (created probably in the EKG/CXR data entry routine) is not present, then one will be created in step (921). The created record will be loaded with data identifying the patient, date of request, date tests completed, lab record invoice, and if from a source encounter then the invoice from that office, E.R. or specialty visit.

After completion of the above, the segment for actual lab record creation, or as the case may be, for simply editing the current blood work tests from an already existent lab record, is entered. FIG. 10 illustrates this routine. Prior to this, however, the operator can access a variety of previous test result data for each lab test to be entered through subroutines findout1.prg and findout2.prg, which are selected through menu options. These subroutines are used for obtaining data from different clinical aspects such as first abnormal data, most abnormal value, most recent result, etc. These two subroutines are illustrated in FIGS. 11 and 12.

Once sufficient prior information for each current test result to be entered is obtained, a customized data entry screen is generated (step 1018) with instructions for operator assistance. This screen allows direct entry of both numeric results and parameter data into each of the indivudial lab test fields to be edited. As in the case of EKG-CXR entry, if a lab test result is normal only two characters are entered: a normal indicator and the most recent result, if present. An example of a source document for entry of lab record (blood work) is given in FIG. 13. Note that unlike the EKG/CXR data entry routine where partial parameter EKG/CXR data is passed to the "companion" lab record, there is no such cross-file processing in the opposite direction. In fact, and as can be seen from the format file used here, the EKG and CXR fields common to both lab and EKG/CXR entry records are "hidden" from view. The only way in which parameter data may be entered into these fields is through the EKG/CXR data entry routine.

Thus, blood work form a "lab test request" is loaded onto an existent lab record previously created, most probably during an EKG/CXR data entry routine for loading results from the same "lab test request". Or the blood work is loaded onto a newly created lab record as the only or first results obtained from a "lab test request" (source or non-source). In either caswe and as in the EKG/CXR entry routine, the lab record is also linked for crossreferencing to any possilble co-existent related EKG/CXR records from the same lab test request. In the case of a source encounter, the lab reocrds are also linked to any of three possible settings (office, E.R., specialist) from which the "lab test request" (blood work and/or CXR/EKG) was made.

3. Print program (print6.prg) for reporting office visit based EKG and/or CXR test results in conjunction with other concurrent clinical data present during the primary care visit in which the tests were ordered.

The purpose of this application is to combine logically distinct but related medical data stored in separate files linked throught common fields. Specifically, this routine links office visit (primary care) records with EKG/CXR records in a "parent to child" relationship. It integrates different and separately stored aspects of clinical data commonly derived in time and place, all centered around the office visit, for a broad composite view of medical care and resource usage. FIG. 14 illustrates the major steps of this program.

Consistent with the underlying thrust of the invention, the clinical data viewed in this report has been generated under a uniform standard set of conditions applied to a population of medical database out-patients in order to establish some reference to facilitate its analysis. This has been accomplished by selecting from a primary file, which stores the compiled results of office visits, only those patient records that meet certain clinical criteria (step 1411). These criteria include characteristics such as a chronic cardiac-based diagnosis as the primary problem during that office visit, presence of any of eight possible single character codes for indicating that at least lab work (in general, a "lab test request") was done, the occurrence of the office visit at least two weeks prior to a controld date, and evidence by code that the patient was symptomatic (or more symptomatic than ususal). Those records selected are then written to a secondary file that will serve as the program's basic unit of information processing.

Each patient's records are processed as a group wherein each page of the generated report represents data from the total number of relevant office visit records on file at that time for that patient. Separate categories of information (such as information from office visits and EKG/CXR) for each patient is delimited by broken lines on the report. The appendix computer listing illustrates example reports generated by this program.

The programs advances though each patient's records and prints general indentifying data once per page. For each office visit the routine prints out data uniquely identifying it (such as by invoice or date) along with patient clinical data. In step (1421) it is determined if EKG and/or CXR tests were ordered during each office visit by searching common data items though both EKG and CXR files. If found the stored subscripts corresponding to the various diagnosis are accessed and used to reference the full descriptive texts from the EKG/CXR table entries stored in memory files. The EKG and/or CXR diagnosis in descriptive text in combination with other data uniquely identifying the EKG/CXR records are formatted along with pertinent clinical data from the "parent" office visit record for detail line printing. In the case where either EXG or CXR tests have been performed, but not both, there is no explicit message in place of any would-be data. But in cases where neither has been done, there is a message. FIGS. 16–22 show reports generated by the program print6.prg.

4. Print program (print7.prg) for reporting out specialist (consultant) recommendations in conjunction with related clinical data from primary care office visits from which the referrals were made.

As in the previous reporting routine, the purpose here is to combine, for the purpose of analysis, logically distinct but related medical information stored in separate files linked by common fields. Namely, this routine integrates primary patient-care data (office visit) with subsequent consultant data in a respectively "parent record" to "child record" relationship. FIG. 15 illustrates the principal steps in this routine.

The list of system specialists include eight conventional types, for instance cardiologist, hematologist, rheumatologist, etc. The recommendations used by the system specialists consists of nine general adivsements of courses of action non-detailed in nature. Each of the nine advisements are to be used as universal standards for all specialists. The advisement include "continue present treatment", "change existing meds", "more lab tests", etc.

As in the previous embodiment (print6.prg), this routine begins by selecting out from a primary file containing compiled office visit data only those patient records that meet a predefined set of clinical criteria in step (1511). These criteria include a chronic cardiac-based condition as the primary problem during the office visit, whether the visit occurred at least 2 weeks prior to a control date, presence of a field code (single character) indicating that a specialty referral was made during that primary care office visit, and whether the patient was symptomatic. These records are then written to a secondary file in which all the records present now serve as the program's basis unit of information processing.

With the file indexed by patient name, the program processes each patient's record as a group. Each page of the report represents one patient and each unit of data delimited by broken lines contains the combined office visit and linked specialty data. There may be more than one specialist visit derived from any previous primary care office visit due either to a follow-up visit or the fact that more than one type of specialist referral was made from any primary care office visit. For each office visit a search is conducted in the specialist file based upon patient and request data. If found, three different specialist data are accessed from that related child record: the type of specialist, the individual specialist recommendations and the specialist's own diagnosis. The type of specialist is accessed by a subscript and expanded to text via a tables of entries containing the descriptive names arranged as an array. The individual specialist recommendations are also stored as subscripts and used to reference their corresponding text descriptive courses of action from a table of entries arranged as an array. The specialist's own diagnoses is referenced by it's six digit code from either the short-term or long term (chronic) diagnostic table depending on that specialist's impression. This information is then formatted with pertinent data from the parent office visit record for printing a composite clinical practice containing both primary care and its related specialty data. FIGS. 23-30 show reports generated by the program print7.prg.

The appendix contains the computer code corresponding to the above described programs.

SCREEN FORMAT: ABN_LAB.FMT

@ 1,0 say "DOCTOR "
@ 1,8 get DOCTOR
@ 1,32 say "PATIENT"
@ 1,40 get PT_ID
@ 2,0 say "DATE REQUESTED"
@ 2,16 get DATEREQEST
@ 2,26 say "SOURCE INVOICE(may be blank)"
@ 2,55 get INVOICEFRM
@ 3,0 say "DATE DONE"
@ 3,11 get datedone
@ 3,26 say "LAB INVOICE"
@ 3,55 get INVOICE
@ 4,0 say "BUN"
@ 4,5 get BUN
@ 4,13 say "CR"
@ 4,16 get CR
@ 4,24 say "HG"
@ 4,27 get HG
@ 4,35 say "HCT"
@ 4,39 get HCT
@ 6,0 say "SED-RATE"
@ 6,9 get SED_RATE
@ 6,18 say "POTTASIUM"
@ 6,29 get POTTASIUM
@ 6,36 say "BLD-SUGAR"
@ 6,46 get BLD_SUG
@ 8,0 say "PH"
@ 8,4 get PH
@ 8,12 say "PO2"
@ 8,16 get PO2
@ 8,25 say "PCO2"

```
@ 8,30 get PCO2
@ 8,38 say "WBC"
@ 8,42 get WBC
@ 10,0 say "CALCIUM"
@ 10,9 get CALCIUM
@ 11,0 say "Press " +CHR(26)+ " or " +CHR(27)+ " to move within fields"
@ 12,0 say "Press " +CHR(24)+ " or " +CHR(25)+ " to move between fields"
@ 13,0 say "Press " + ret + " to finish data entry and move to next field"
@ 14,0 say "when at last/tiny field,press " + ret + " to REMAIN/RECHECK"
@ 15,0 say "if you decide against doing blood work,press Y/y"
@ 16,0 say "if everything is o.k. and your finished,press X/x"
@ 16,52 get mdone
```

SCREEN FORMATS: EKGCXRFM.FMT

```
clear
@ 3,5 say "patient id no"
@ 3,20 say mpt_id
@ 4,5 say "date test requested"
@ 4,25 say dater
@ 5,5 say "date test was done"
@ 5,24 say dated
@ 7,5 say "source invoice(may be blank)"
@ 7,34 say minvoice
@ 9,5 say "these are the item no.'s from the menu"
@ 9,44 say mcar
@ 10,5 say "remember,if there is just a 1(normal)"
@ 11,5 say "then just enter a T in length field only!"
@ 12,5 say "now enter the three parameter codes according"
@ 13,5 say "to the system instructions(HELP FILE)"
@ 14,2 say "length(A,S,C)   intensity(1,2,3,4)   comparison(I,W,N,U,P)"
@ 14,15 get mlen
@ 14,37 get minten
@ 14,61 get mcomp
@ 16,5 say "to quit when done press X/x"
@ 17,5 say "to retry/recheck press" + ret
@ 17,34 get mdone picture "A"
```

CREATREC.PRG (TEXT FORMAT)

```
public  dater,mpt_id,minvoice,mflagy,mflagx,hold,mpar,mlen,mflagz,here
do while .t.
 mlen = space(1)
 minten = space(1)
 mcomp = space(1)
 padding = "000000"
 minv = space(6)
 mflagz = .f.
 minvoice1 = "L00000"
 minvoice = space(6)
 mflag2 = space(1)
 mpt_id = space(11)
 dated = ctod(" / / ")
 dater = ctod(" / / ")
 clear
 @ 5,0 say "please enter pt. id. no.,request date,and date done"
 @ 6,14 get mpt_id picture "999-99-9999"
 @ 6,26 get dater
 @ 6,35 get dated
do while upper(mflag2) <> "O" .and. upper(mflag2) <> "E" .and.
upper(mflag2) <> "Q" .and. upper(mflag2) <> "N" .and. upper(mflag2)
<> "S"
 @ 7,0 say "now, if source(origin) of the test was office"
 @ 8,0 say "enter(O/o)E.R.enter(E/e),SPECIALISTenter(S/s)"
 @ 9,0 say "if NO SOURCE indicated,enter(N/n).Then wait 1 min"
 @ 10,0 say "If you want to quit,enter(Q/q)"
 @ 10,32 get mflag2 picture "A"
 read
enddo
if upper(mflag2) = "Q"
 clear
 return
endif
mflagy = .f.
if upper(mflag2) <> "N"
if upper(mflag2) = "O"
 use encountf index patdat
 seek mpt_id + dtoc(dater)
 store invoice to minvoice
endif
if upper(mflag2) = "E"
```

```
use er_room index patdater
seek mpt_id + dtoc(dater)
store invoice to minvoice
endif
if upper(mflag2) = "S"
 use specalst index patdats
 seek mpt_id + dtoc(dater)
 store invoice to minvoice
endif
if .not. found()
 clear
 @ 5,5 say "record from request date not done,or wrong"
 @ 6,5 say "data,so you can't create new record now."
 @ 7,5 say "start over,another patient,or quit"
 wait
 loop
endif
else
 use abn_laba index patdatr,ablbinvf
 seek mpt_id + dtoc(dater)
 if found()
  if invoicefrm = space(6)
   store .t. to mflagy
   hold = recno()
  endif
 endif
 use
endif
use abn_laba index ablbinvf,patdatr
store .f. to mflagx
if minvoice <> space(6)
seek minvoice
 if found()
 store .t. to mflagx
 endif
endif
if .not. mflagx .and. .not. mflagy
 set order to 0
 goto bottom
 store substr(invoice,2,5) to minv
 store val(minv) + 1 to minv
 store stuff(minvoice1,2,5, right(padding + ltrim(str(minv,5)),5)) to
```

```
minvoice1
  append blank
  replace pt_id with mpt_id
  replace invoice with minvoice1
  replace invoicefrm with minvoice
  replace datereqest with dater
  hold = recno()
  set index to ablbinvf,patdatr
  reindex
endif
use
do while .t.
 mchoice = space(1)
 clear
 @ 9,0 say "search pt's prior lab data first(A)"
 @ 10,0 say "would you like help?(B)"
 @ 11,0 say "you searched,now enter encoded data(C)"
 @ 12,0 say "leave the routine?(D)"
 @ 13,0 say "make selection here" get mchoice
 read
 if upper(mchoice) $ "ABCD"
  if upper(mchoice) = "C"
   if .not. mflagz
    store .t. to mflagz
   else
    clear
    @ 5,5 say "already created a record for this patient"
    @ 6,5 say "for another record(cxr/ekg) or patient"
    @ 7,5 say "you must return to the beginning"
    wait
    store .f. to mflagz
    clear
    return
   endif
   mdone = space(1)
   ret = chr(17)+chr(196)+chr(217)
   clear
   if upper(mflag) = "E"
    use ekgrec index patient,patdatek
   else
    use cxrrec index patientc,patdatcx
   endif
   set format to ekgcxrfm
```

```
do while .t.
 read save
 if upper(mdone) = "X"
   mchoice = space(1)
   exit
 else
  loop
 endif
enddo
mpar=""
store mpar + mlen to mpar
store mpar + minten to mpar
store mpar + mcomp to mpar
append blank
replace datedone with dated
replace pt_id with mpt_id
replace invoicefrm with minvoice
replace diagfield with mcar
replace parafield with mpar
replace datereqest with dater
here = recno()
reindex
use
close format
clear
loop
endif
if upper(mchoice) = "B"
 do mmessage
 loop
endif
if upper(mchoice) = "D"
 return
endif
if upper(mchoice) = "A"
  do while .t.
  msel = 0
  clear
   @ 9,0 say "date and value of first abnormality(1)"
   @ 10,0 say "date and value of last abnormality(2)"
   @ 11,0 say "is test consistently abnormal?(3)"
   @ 12,0 say "latest entry for that test(4)"
   @ 13,0 say "leave search for code entry(5)"
```

```
     @ 13,32 get msel picture "9"
     read
     if msel = 5
     clear
exit
     endif
     if ltrim(str(msel)) $ "1234"
      if ltrim(str(msel)) $ "12"
       do find1
      else
       do find2
      endif
     endif
    enddo
   endif
  else
   clear
   @ 5,5 say "try again,you hit a wrong key!"
   wait
  endif
 enddo
enddo
```

MMESSAGE.PRG (TEXT FORMAT)

text
          HOW TO ENTER THE LAB RECORD
Each field of the record you will create corresponds to an;individual laboratory test. Any test may or may not be done at;any given time. The format you will use for entering the encoded;data will depend upon the results(normal/abnormal) and maybe ;whether or not the test was done at all.
A full-field data entry(7 characters wide) is done only with;abnormal lab values.Otherwise,in the event of a normal result,a;"T" is entered into the first character position and then one;of three capital letters: A,B,or C, is entered into the FOURTH; position depending upon whether or not,respectively,the most;  recent entry was normal(A),abnormal(B),or not done(found) at;  all(C).
endtext
wait
text
For every test that is left blank on the lab report form(not
done),an N is to be placed into the first character position,
if,and only if,that particular test has been abnormal for that patient in the past.The N will indicate to the system of a "pending abnormality". This,and other information,will be made
available to you through selecting from a menu of routines present further along in this program.
endtext
wait
text
   For ABNORMAL values:the first three charcters constitute the encoded segment. The first position will contain one of four possible characters that will indicate the duration of that test's abnormality: A if present less than 3 mos.,S if present
3 to 6 mos.,C if present > 6 mos.,an I will be entered if it has not been consistently abnormal. The second character position will contain one of four possible 'numbers'(character data) to indicate extent or degree of abnormality.(It is here that the
operator's discretion must be used.) A 1 is entered for "very high",a 2 for moderately high,a 3 for very low,and a 4 for moderately low. For example;a blood sugar of 210 is moderately
high(2),but one of >350 would be very high(1). A hg of 10.1 or 9.9 might be moderately low(4),but one of 7.3 is very low(3).
endtext
wait
text
The third position is for comparative(historical) data; if the abnormal value has improved from the last entry, an I is entered.
If essentially unchanged(~ < 5%),then a U is entered. If worsened, (higher in the case of blood sugar,or lower in the case of hg,e.t.c.) then a W is entered.And,an N is entered if that abnormal te'st is the first on record.The last four positions will contain the
actual "numerical" quantities,including decimals(the system will 'treat' them as character data) However,for the "WBC" test,the number will be rounded from the lab report to the nearest thousandth and a "x3" will be appended by you. For example,
a count of 13,650 will be entered as 14x3, a count of 13,450 will be entered as 13x3.e.t.c.
                    name field
EXAMPLE OF ABNORMAL RECORD: BUN  C2U31.4
this indicates a CHRONIC abnormality,MODERATELY elevated,and UNCHANGED(essentially) from previous. These three determinations will(can) be made from the menu selections at another place in the program. The last 4 characters(quantity) is to be taken directly from the lab report.
endtext

```
wait
text
                    name field
EXAMPLE OF NORMAL RECORD: BUN  T B
the T is to indicate a normal result and the B in the fourth character
position is to indicate that the most previous test
was abnormal.Naturally,the decision to enter the T is made from
the lab report,but the "previous test" information is determined
by selecting the appropriate routine from the menu. Remember,
if there isn't any prior record of that test(normal or abnormal),
you must enter a C into the fourth position.

EXAMPLE FOR A BLANK FIELD(on the lab report)
(only if the LATEST entry is ABNORMAL,not a normal one)
   name field
   BUN  N_____   the underscore characters were included here to
emphasize that in this case,just an N in position one and leave
the rest of the field blank.
endtext
wait
text
All the necessary information about each lab test that is needed
for accurate data entry is available through the menu-derived
routines.If you wish to review this,press "B" again when you return to the
menu ENDTEXT
wait
return

FIND1.PRG (TEXT FORMAT)

public mpt_id,hello
clear
mvar1 = ""
mvar2 = ""
mdate = ctod(" / / ")
store ctod(" / / ") to mdate1,mdate2,mdate4
if upper(mflag) = "E"
 use ekgrec index patient
else
 use cxrrec index patientc
endif
seek mpt_id
```

```
if .not. found()
 @ 5,5 say "no records for this patient on file"
 wait
 return
endif
hello= recno()
skip 1
if eof() .or. PT_ID <> mpt_id
 @ 1,0 say "this is only record! so just review"
 wait
 return
else
 goto hello
 store DATEDONE to mdate
endif
 do while .t.
  do case
   case ltrim(str(msel)) = "1"
    do while PT_ID = mpt_id
    store field(5) to mvar
    store &mvar to mvar1
      if substr(mvar1,1,1) <> "T"
       store field(6) to mvar2
       store &mvar2 to mvar3
       store DATEDONE to mdate2
       use
       exit
      else
       skip
       if eof()
        exit
       endif
       loop
      endif
    enddo
    if asc(mvar1) = 84
 @ 2,0 say "no abnormal records since " + dtoc(mdate)
else
 mline = 5
 mcount = 1
 mnum = 1

@ mline,0 say "first abnormal record " + dtoc(mdate2)
```

```
  do while mcount <= len(rtrim(mvar3))/2
   store substr(mvar3,mnum,2) to mvar4
   store ltrim(mvar4) to mvar5
   @ mline + 1,0 say opt&mvar5
   mline = mline + 1
   mnum = mnum + 2
   mcount = mcount+1
  enddo
  wait
  use
return
case ltrim(str(msel)) = "2"
 do while PT_ID = mpt_id
   store field(5) to mvar
   store &mvar to mvar1
   store datedone to mdate1
   if substr(mvar1,1,1) <> "T"
    store field(6) to mvar2
    store &mvar2 to mvar3
    store DATEDONE to mdate2
    skip
    if eof()
     exit
    endif
    loop
   else
    skip
    if eof()
     exit
    endif
    loop
   endif
 enddo
 use
 if len(mvar2) = 0
   @ 2,0 say "normal ekg's,last test " + dtoc(mdate1)
   wait
   return
 else
   mline = 5
   mcount = 1
```

```
   mnum = 1
   @ mline,0 say "last abnormal record " + dtoc(mdate2)
   do while mcount <= len(rtrim(mvar3))/2
    store substr(mvar3,mnum,2) to mvar4
    store ltrim(mvar4) to mvar5
    @ mline + 1,0 say opt&mvar5
    mline = mline + 1
    mnum = mnum + 2
    mcount = mcount + 1
   enddo
  endif
  wait
  return
 endcase
endo
use
return

FIND2.PRG (TEXT FORMAT)

public mpt_id,hello
clear
mdate = ctod(" / / ")
store ctod(" / / ") to mdate1,mdate2,mdate4
if upper(mflag) = "E"
 use ekgrec index patient
else
 use cxrrec index patientc
endif
seek mpt_id
if .not. found()
 @ 5,5 say "no records for this patient on file"
 wait
 clear
 return
endif
hello = recno()
skip 1
if eof() .or. PT_ID <> mpt_id
 @ 1,0 say "this is only record!,so just review"
 wait
 return
else
```

```
     goto hello
  endif
   do while .t.
     do case
        case ltrim(str(msel)) = "3"
          store .f. to mflagk
          store 0 to mcount,mcount1
          do while PT_ID = mpt_id
            store field(5) to mvar
            store &mvar to mvar1
            if substr(mvar1,1,1) = "T"
              store mcount1 + 1 to mcount1
              store DATEDONE to mdate1
              skip
              if eof()
                exit
              endif
              loop
            endif
            if asc(mvar1) <> 78 .and. substr(mvar1,1,1) <> "T"
              store mcount + 1 to mcount
              if .not. mflagk
                store DATEDONE to mdate2
                store .t. to mflagk
              endif
              skip
              if eof()
                exit
              endif
              loop
            else
              skip
              if eof()
                exit
              endif
              loop
            endif
          else
            skip
            if eof()
              exit
            endif
            loop
          endif
```

```
enddo
use
if mcount = 0 .and. mcount1 <> 0
  @ 2,0 say rtrim(mvar) + " has never been found abnormal"
  @ 3,0 say "it was last found normal on " + dtoc(mdate1)
  wait
  return
endif
if mcount <> 0 .and. mcount1 = 0
  @ 2,0 say rtrim(mvar) + " has been consistently abnormal since "
+ dtoc(mdate2) + " " + str(mcount) + " time(s)"
  wait
  return
endif
if mcount <> 0 .and. mcount1 <> 0
  @ 2,0 say rtrim(mvar) + " has been intermittently abnormal"
  @ 3,0 say "the last date it was normal was on:" + dtoc(mdate1)
  wait
  return
endif
if mcount = 0 .and. mcount1 = 0
  @ 2,0 say rtrim(mvar) + " has never been drawn"
  wait
  return
endif case ltrim(str(msel)) = "4"
  do while pt_id = mpt_id
    skip
  enddo
  skip - 1
  store datedone to mdate4
  store field(5) to mvar
  store &mvar to mvar1
  store field(6) to mvar2
  store &mvar2 to mvar3
  if substr(mvar1,1,1) <> "T"
    mline = 5
    mcount = 1
    mnum = 1
    @ mline,0 say "the latest entry for that test was:" + dtoc(mdate4)
    do while mcount <= len(rtrim(mvar3))/2
      store substr(mvar3,mnum,2) to mvar4
```

```
    store ltrim(mvar4) to mvar5
    @ mline + 1,0 say opt&mvar5
    mline = mline + 1
    mnum = mnum + 2
    mcount = mcount + 1
   enddo
   wait
   use
   return
  endif if substr(mvar1,1,1) = "T"
    @ 2,0 say "the latest entry was normal on " + dtoc(mdate4)
    wait
    return
   endif
  endcase
 enddo
 use
 return
```

MENU.PRG (TEXT FORMAT)

```
procedure litebar
parameters opno,menutitle,mcar
set talk off
set status off
clear
row = 5
@ 1,1 to 3,78 double
@ 2,22 say menutitle @ 20,1 to 24,78 double
@ 22,18 say "highlight option with"
@ 22,40 say chr(24)+" or "+chr(25)+" and press "+chr(17)+chr(217)
@ 23,22 say "to enter that selection number"

@ 4,30
row = 5
do while row-4<=opno
 sub = iif(row-4 > 9,str(row-4,2),str(row-4,1))
 opt&sub = iif(row-4 > 9,str(row-4,2)+". "+opt&sub,str(row-4,1)+". "+opt&sub)
```

```
  @ row,30 say opt&sub
  row=row+1
enddo opt=1
sub="1"
sel=0

@ 5,30 get opt1
clear gets
mcount = 1 do while mcount <= 4
  sel = 0
  do while sel = 0
  sel = inkey()
  enddo if sel=24 .or. sel=5
    @ opt+4,30 say opt&sub
    opt=IIF(sel=24,opt+1,opt-1)
    opt=IIF(opt>opno,1,opt)
    opt=IIF(opt<1,opno,opt)
    sub=iif(opt>9,str(opt,2),str(opt,1))
    @opt+4,30 get opt&sub
    clear gets
    loop
  endif
  if sel = 13
   if opt = 15
    return
    else
    store mcar + str(opt,2) to mcar
    mcount = mcount + 1
    endif
   else
   loop
   endif
enddo
return
procedure ekgproc
parameters mcard,mflag1
clear
```

```
@ 1,0 say "these are your selections"
mline = 3
mnum = 1
private mcount
mcount = 1
do while mcount <= len(mcard)/2
 store substr(mcard,mnum,2) to mvar
 store ltrim(mvar) to mvar1
 @ mline,5 say opt&mvar1
 mline = mline + 1
 mnum = mnum + 2
 mcount = mcount + 1
enddo
wait
mflag1 = space(1)
do while upper(mflag1) <> "C" .and. upper(mflag1) <> "S"
@ mline + 2,0 say "if correct,then proceed by pressing(C/c)"
@ mline + 3,0 say "if not,then press (S/s) to start over"
@ mline + 3,39 get mflag1
read
enddo
 if upper(mflag1) = "S"
   clear
   return
 endif
 if upper(mflag1) = "C"
   clear
   store mcard to mcar
   do creatrec
 endif
clear
return
```

LABFIRST.PRG (TEXT FORMAT)

```
public mpt_id,mv,minvoice,mdate
set talk off
do while .t.
padding = "000000"
mv = space(6)
minvoice1 = "L00000"
minvoice = space(6)
dated = ctod(" / / ")
```

```
dater = ctod(" / / ")
mflag2 = space(1)
mpt_id = space(11)
clear
@ 1,0 say "THIS IS THE PATIENT LAB RECORD ENTRY AND INQUIRY ROUTINE "
@ 2,0 say " enter patient i.d. no.,request date,and datedone"

@ 3,14 get mpt_id picture "999-99-9999"
@ 3,26 get dater
@ 3,40 get dated
do while upper(mflag2) <> "O" .and. upper(mflag2) <> "E" .and.
upper(mflag2) <> "N" .and. upper(mflag2) <> "Q" .and. upper(mflag2)
<> "S"
@ 4,0 say "to leave fields blank,press down arrow"
@ 5,0 say "until you reach the last one"
@ 6,0 say "now,if source(origin) of the test was office"
@ 7,0 say "enter(O/o),if E.R.enterE/e,SPECIALTY enterS/s"
@ 8,0 say "if NO SOURCE indicated,enter(N/n). Then wait 1 min."
@ 9,0 say "if you want to quit,enter(Q/q)"
@ 9,32 get mflag2
read
enddo
if upper(mflag2) = "Q"
 clear
 return
endif
mflagy = .f.
mflagx = .f.
if upper(mflag2) <> "N"
 if upper(mflag2) = "O"
  use encountf index patdat
   seek mpt_id + dtoc(dater)
   if .not. found()
    clear
    @ 2,2 say "off.record not done?bad data? try again"
    wait
    loop
   endif
   store invoice to minvoice
endif
if upper(mflag2) = "E" use er_room index patdater
  seek mpt_id + dtoc(dater)
```

```
    if .not. found()
      clear
      @ 2,2 say "e.r.record not done?bad data? try again"
      wait
      loop
    endif
    store invoice to minvoice
  endif
  if upper(mflag2) = "S"
   use specalst index patdats
    seek mpt_id + dtoc(dater)
    if .not. found()
      clear
      @ 2,2 say "specialist record not yet done?bad data?"
      wait
      loop
    endif
    store invoice to minvoice
  endif
 else
  use abn_laba index patdatr,ablbinvf
   seek mpt_id + dtoc(dater)
   if found()
    if invoicefrm = space(6)
      store .t. to mflagy
      hold = recno()
    endif
   endif
  use
 endif
 use abn_laba index ablbinvf,patdatr
 store .f. to mflagx
 if minvoice <> space(6)
  seek minvoice
   if found()
    store .t. to mflagx
    store invoice to minvoice1
    hold = recno()
   endif
 endif
 if .not. mflagx .and. .not. mflagy
  set order to 0
  goto bottom
  store substr(invoice,2,5) to minv
```

```
    store val(minv) + 1 to minv
    store stuff(minvoice1,2,5, right(padding + ltrim(str(minv,5)),5)) to
minvoice1
   append blank
   replace pt_id with mpt_id
   replace invoice with minvoice1
   replace invoicefrm with minvoice
   replace datedone with dated
   replace dateregest with dater
   hold = recno()
   set index to ablbinvf,patdatr,abnpatinv,patientl
   reindex
 endif
 do labentry
 close format
 if upper(mdone) = "Y"
  if .not. mflagx .and. .not. mflagy
   use abn_laba index ablbinvf,abnpatin,patientl,patdatr
   goto hold
   delete
   pack
   reindex
  endif
 endif
 close all
enddo

FINDOUT1.PRG (TEXT FORMAT)

public mpt_id,mtest,mchoice,minvoice,hello
clear
mdate = ctod(" / / ")
store ctod(" / / ") to mdate1,mdate2,mdate4
use abn_laba index abnpatin,patientl
seek mpt_id + minvoice1
skip - 1
if bof() .or. PT_ID <> mpt_id
 @ 1,0 say "this is first record!,you can't search"
 wait
 return
else
 store DATEDONE to mdate
 @ 1,0 say "DATE OF LAST RECORD IS:" + dtoc(mdate)
 wait
```

```
  set order to 2
  seek mpt_id
endif
do while .t.
  do case
    case mchoice = "1"
      store .f. to mflag
      do while PT_ID = mpt_id .and. INVOICE <> minvoice1
      store field(mtest) to mvar
      store &mvar to mvar1
        if asc(mvar1) <> 32 .and. substr(mvar1,1,1) <> "T"
        .and. asc(mvar1) <> 78
        store .t. to mflag
        store DATEDONE to mdate2
        @ 2,0 say "INQUIRY OF LAB TEST:" + mvar
        @ 3,0 say "DATE OF FIRST ABNORMALITY:" + dtoc(mdate2)
        if mtest = 19 .or. mtest = 20
          if substr(mvar1,2,1) = "1"
            @ 4,0 say "VALUE OF ABNORMALITY:very abnormal"
          else
            @ 4,0 say "VALUE OF ABNORMALITY:mildly abnormal"
          endif
        else
          @ 4,0 say "VALUE OF FIRST ABNORMALITY:" + substr(mvar1,4,4)
        endif
        wait
        exit
      else
       skip
       if eof()
        exit
       endif
       loop
      endif
     enddo
     if .not. mflag
         @ 2,0 say "that lab test is not on record as abnormal"
      wait
      return
     endif
     exit
    case mchoice = "2"
      store .f. to mflag
```

```
do while PT_ID = mpt_id .and. INVOICE <> minvoice1
   store field(mtest) to mvar
   store &mvar to mvar1
   if asc(mvar1) <> 32 .and. asc(mvar1) <> 78
         .and. substr(mvar1,1,1) <> "T"
     store mvar1 to mvar2
     store DATEDONE to mdate2
     store .t. to mflag
     skip
     if eof()
      exit
     endif
     loop
   else
     skip
     if eof()
      exit
     endif
     loop
   endif
enddo
if mflag
  @ 2,0 say "INQUIRY OF LAB TEST:" + mvar
  @ 3,0 say "DATE OF LATEST ABNORMALITY:" + dtoc(mdate2)
  if mtest = 19 .or. mtest = 20
    if substr(mvar1,2,1) = "1"
     @ 4,0 say "VALUE OF ABNORMALITY:very abnormal"
    else
     @ 4,0 say "VALUE OF ABNORMALITY:mildly abnormal"
    endif
  else
  @ 4,0 say "VALUE OF LATEST ABNORMALITY:" + substr(mvar2,4,4)
  endif
  wait
  return
else
        @ 1,0 say "LAB TEST " + mvar1 + "is not on file as abnormal"
   wait
   return
  endif
 endcase
enddo
use
return
```

LABENTRY.PRG (TEXT FORMAT)

```
public mpt_id,mtest,minvl,mchoice,hello,minvoice,mdate,mdone
store 0 to mtest
mselect = space(1)
DO while .t.
  store " " to mselect
  clear
  @ 1,0 say "SELECT FROM ONE OF THE FOUR CHOICES BELOW BY"
  @ 2,0 say "PRESSING ONE OF THE FOUR LETTERS:A,B,C(or D TO QUIT)"
  @ 3,0 say "THAT ARE ASSOCIATED WITH EACH CHOICE."
  @ 4,0 say replicate ("=",66)
  @ 5,0 say "ARE YOU READY TO ENTER DATA IN ENCODED FORM? (A)"
  @ 6,0 say "WOULD YOU LIKE HELP? (B)"
  @ 7,0 say "DO YOU WISH TO SEARCH PATIENT'S PRIOR LAB DATA FIRST? (C)"
  @ 8,0 say "DO YOU WISH TO LEAVE/QUIT? (D)"
  @ 9,0 say "make your selection here" get mselect
  read
  if upper(mselect) $ "ABCD"
  if upper(mselect) = "A"
   mdone = space(1)
   ret = chr(17)+chr(196)+chr(217)
   clear
   use abn_laba
   do case
    case .not. mflagx .and. .not. mflagy
    goto hold
    replace datedone with dated
    case mflagy
    goto hold
    replace datedone with dated
    otherwise
    set index to ablbinvf
    seek minvoice
    replace datedone with dated
   endcase
   set format to abn_lab
   do while .t.
    read save
    if upper(mdone) = "Y"
     return
    endif
```

```
if upper(mdone) = "X"
 mselect = space(1)
 exit
else
 loop
endif
  enddo
  close format
  use
  clear
  loop
 endif
 if upper(mselect) = "B"
   do mmessage
   loop
 endif
 if upper(mselect) = "D"
  clear
  @ 1,0 say "ARE YOU SURE YOU HAVE ENTERED THE DATA ?!"
  @ 2,0 say "if you have forgotten,"
  store " " to yesno
  do while .not. upper(yesno) $ "YN"
  wait "press Y/y to return to menu or N/n to leave" to yesno
  enddo
  if upper(yesno) = "Y"
   loop
  else
   clear
   return
  endif
 endif
 if upper(mselect) = "C"
  mtest = 0
  mchoice = space(1)
  do while upper(mchoice) <> "5"
  mchoice = space(1)
  clear
  @ 1,0 say "SELECT ONE OF THE FOLLOWING LAB TESTS BY THE"
  @ 2,0 say "NUMBER IN PARENTHESIS ASSOCIATED WITH THE TEST NAME."
   @ 3,0 say replicate("=",66)
   @ 4,0 say "BUN(7)"
   @ 4,7 say "CR(8)"
```

```
@ 4,13 say "HG(9)"
@ 4,19 say "HCT(10)"
@ 4,26 say "SEDRATE(11)"
@ 4,38 say "POTTASIUM(12)"
@ 4,52 say "BLD SUGAR(13)"
@ 5,0 say "PH(14)"
@ 5,7 say "PO2(15)"
@ 5,15 say "PCO2(16)"
@ 5,24 say "WBC(17)"
@ 5,32 say "CALCIUM(18)"
@ 6,0 say "please select one of the above, or enter 21"
@ 7,0 say "in order to leave/quit" get mtest picture "@Z 99"
read
 if mtest = 21
  exit
 endif
 if mtest < 7 .or. mtest > 20
   clear
   @ 1,0 say "wrong key pressed,please repeat"
   wait
   loop
 else
  do while .t.
  store " " to mchoice
  @ 8,0 say "NOW SELECT THE KIND OF PREVIOUS INFORMATION"
  @ 9,0 say "YOU WANT ABOUT THAT LAB VALUE BY SELECTING"
  @ 10,0 say "THE ASSOCIATED NUMBER IN PARENTHESIS."
  @ 11,0 say replicate("=",66)
  @ 12,0 say "DATE AND VALUE OF FIRST ABNORMALITY (1)"
  @ 13,0 say "DATE AND VALUE OF LAST ABNORMALITY (2)"
  @ 14,0 say "IS THE TEST CONSISTENTLY ABNORMAL? (3)"
  @ 15,0 say "LATEST ENTRY FOR THAT TEST(normal/abnormal) (4)"
  @ 16,0 say "CHOOSE (5) to leave/choose another test"
  @ 17,0 say "please make selection here" get mchoice
  read
  if mchoice = "5"
   exit
  endif
  if mchoice $ "1234"
   if mchoice $ "12"
    do findout1
    store " " to mchoice
    loop
```

```
    else
     do findout2
     store " " to mchoice
     loop
    endif
   else
    @ 18,0 say "wrong key pressed,press either 1,2,3,4 or 5"
    wait
    loop
   endif
  enddo
  endif
 enddo
endif
else
 clear
 @ 1,0 say "wrong key pressed,please repeat"
 wait
 loop
endif
enddo
return
public mpt_id,rdate,ddate,mcar,mflag
set talk off
set status off
set procedure to menu
use abn_laba index ablbinvf,patdatr
reindex
use
clear
do while .t.
  mflag = space(1)
  do while upper(mflag) <> "E" .and. upper(mflag) <> "C" .and. upper(mflag) <> "Q"
    @ 5,0 say "do you want to do ekg records(press E/e) or"
    @ 6,0 say "cxr records(press C/c)? If both,then please"
    @ 7,0 say "do one at a time. for BOTH same or different"
    @ 8,0 say "patients. To quit press Q/q"
    @ 8,28 get mflag picture "A"
    read
  enddo
  if upper(mflag) = "Q"
```

```
    use abn_laba index ablbinvf,patdatr
    reindex
use ekgrec index patdatek,patient
reindex
use cxrrec index patdatcx,patientc
reindex
close databases
close proc
clear
return
endif
mcar = ""
mflag1 = space(1)
if upper(mflag) = "E"
  opt1 = "within normal limits"
  opt2 = "shortened pr interval"
  opt3 = "prolonged pr interval"
  opt4 = "chr. ant. wall ischemia"
  opt5 = "chr. lat. wall ischemia"
  opt6 = "chr. inf. wall ischemia"
  opt7 = "biventr.hypertrophy"
  opt8 = "pvc's multifocal"
  opt9 = "pvc's unifocal"
  opt10 = "flat(tening) t waves"
  opt11 = "u waves"
  opt12 = "acute ant. wall isch."
  opt13 = "acute inf. wall isch."
  opt14 = "acute lat. wall isch."
  opt15 = "exit this routine"
  thistitle = "EKG RECORD ENTRY(max. of 4 selections)"
else
  opt1 = "within normal limits"
  opt2 = "mod(r)lung infiltrate"
  opt3 = "mod(l)lung infiltrate"
  opt4 = "bilateral infiltrates"
  opt5 = "ext. infiltrates(r+l)"
  opt6 = "ext.infiltrate(r)"
  opt7 = "ext.infiltrate(l)"
  opt8 = "single lesion(r)"
  opt9 = "single lesion(l)"
  opt10 = "incr. pulm.vasc."
  opt11 = "prob. pulm. edema."
  opt12 = "bilat.cardiomegaly"
```

```
  opt13 = "left vent.hyper."
  opt14 = "right vent. hyper."
  opt15 = "exit this routine"
  thistitle = "CXR RECORD ENTRY(max. of 4 selections)"
endif
set color to GR+/B,W+/BR,G
options = 15
do litebar with options,thistitle,mcar
clear
 if len(mcar) > 0 .and. len(mcar) <= 8
   do ekgproc with mcar,mflag1
   if upper(mflag1) = "S"
    loop
   endif
 endif
 if len(mcar) > 8
   @ 1,0 say "you selected more than the max!(4)"
   @ 2,0 say "you must start over"
   wait
   store "" to mcar
   loop
 endif
 if len(mcar) = 0
   @ 1,0 say "you didn't choose any"
   @ 2,0 say "you must start over"
   loop
 endif
endif
mwhat = ""
if upper(mlen) = "T"
 if upper(mflag) = "E"
   use ekgrec index patdatek
 else
   use cxrrec index patdatcx
 endif
seek mpt_id + dtoc(dater)
skip - 1
if pt_id = mpt_id
 if substr(parafield,1,1) = "T"
   store "B" to mwhat
   skip
   replace diagfield with "B"
 else
```

```
    store "A" to mwhat
    skip
    replace diagfield with "A"
   endif
  else
   store "C" to mwhat
   skip
   replace diagfield with "C"
  endif
 endif
 use abn_laba
 do case
 case .not. mflagy .and. .not. mflagx
  goto hold
 case mflagy
  goto hold
 otherwise
  set index to ablbinvf
  seek minvoice
 endcase
 if upper(mflag) = "E"
  replace ekg with mpar + mwhat
 else
  replace cxr with mpar + mwhat
 endif
 use
enddo
msysdate = ctod("05/01/87")
store ctod(" / / ") to mdate
mtitle1 = "CHRONIC PROBLEM ekg and/or cxr data for"
mtitle2 = "unstable cardiac patients(all categories)"
set device to print
select a
use notify1 index patient
append from notify for msysdate - date >= 14 .and. substr(category,6,1)
$   "EFGHMNOP"   .and.   substr(category,3,1)   <>   "1"   .and.
substr(condition,2,1) = "H" .and. code = "f"
goto top
reindex
select b
use ekgrec index patdatek
select c
use cxrrec index patdatcx
```

```
select d
use chrmedli index chrcode
select a
goto top
do while .not. eof()
 @ 1,(85 - len(mtitle1))/2 say mtitle1
 @ 2,(85 - len(mtitle2))/2 say mtitle2
 @ 3,0 say replicate("=",80)
 store pt_id to mpt_id
 @ 4,0 say "PATIENT ID:" + mpt_id + " CLINICAL CATEGORY(prim.dx.):"
+ substr(category,1,1)
 @ 5,0 say replicate("=",80)
 mline = 6
 do while pt_id = mpt_id
  do case
   case substr(category,3,1) = "2"
    store "2(mild sx.)" to mstatus
   case substr(category,3,1) = "3"
    store "3(sev. sx.)" to mstatus
   case substr(category,3,1) = "4"
    store "4(imprvmnt)" to mstatus
   case substr(category,3,1) = "5"
    store "5(hospital)" to mstatus
  endcase
  mvar1 = space(8)
  mvar2 = space(8)
  store condition to mcondition
  select d
  seek mcondition
  store descript to mdes
  select b
  seek mpt_id + dtoc(notify1->date)
  if found()
   if substr(parafield,1,1) = "T"
    store "T" to mvar1
   else
    store diagfield to mvar1
    store rtrim(mvar1) to mvara
   endif
  endif
  select c
  seek mpt_id + dtoc(notify1->date)
  if found()
```

```
  if substr(parafield,1,1) = "T"
   store "T" to mvar2
  else
   store diagfield to mvar2
   store rtrim(mvar2) to mvarb
  endif
 endif
 if mline >= 56
  @ 1,0 say
  @ 2,0 say
  @ 3,0 say replicate
  @ 4,0 say "PATIENT " + pt_id + "(continued)
  @ 5,0 say replicate("-",80)
  mline = 6
 endif
 if mvar1 <> space(8) .or. mvar2 <> space(8)
  @ mline,0 say "OFFICE DATE:" + dtoc(notify1->date) + " STATUS:" +
mstatus + " PRIM.OFF.DX:" + rtrim(mdes)
  mline = mline + 1
  if mvar1 <> space(8)
   if substr(mvar1,1,1) = "T"
    @ mline,0 say "EKG:WITHIN NORMAL LIMITS" + " DATE DONE:" +
dtoc(ekgrec->datedone) + " INVOICE:" + ekgrec->invoicefrm
    mline = mline + 1
   else
   restore from heart additive
   mcount = 1
   mnum = 1
   @ mline,0 say "THE EKG DIAGNOSIS(es) " + "DATE DONE:" +
dtoc(ekgrec->datedone) + " INVOICE:" + ekgrec->invoicefrm
   mline = mline + 1
   do while mcount <= len(mvara)/2
    if mcount = 1
     mcol = 0
    endif
    if mcount = 2
     mcol = 30
    endif
    if mcount > 2
     if mcount = 3
      mline = mline + 1
      mcol = 0
     else
```

```
      mcol = 30
     endif
    endif
    store ltrim(substr(mvara,mnum,2)) to mvarx
    @ mline,mcol say car&mvarx
    mcount = mcount + 1
    mnum = mnum + 2
   enddo
   mline = mline + 1
  endif
 endif
 if mvar2 <> space(8)
  if substr(mvar2,1,1) = "T"
   @ mline,0 say "CXR:WITHIN NORMAL LIMITS" + "DATEDONE:" + dtoc(cxrrec->datedone) + " INVOICE:" + cxrrec->invoicefrm
   mline = mline + 1
  else
  restore from lung additive
  mcount = 1
  mnum = 1
  @ mline,0 say "THE CXR DIAGNOSIS(es) " + "DATE DONE:" + dtoc(cxrrec->datedone) + " INVOICE:" + cxrrec->invoicefrm
   mline = mline + 1
   do while mcount <= len(mvarb)/2
    if mcount = 1
     mcol = 0
    endif
    if mcount = 2
     mcol = 30
    endif
    if mcount > 2
     if mcount = 3
      mline = mline + 1
      mcol = 0
     else
      mcol = 30
     endif
    endif
    store ltrim(substr(mvarb,mnum,2)) to mvary
    @ mline,mcol say lun&mvary
    mcount = mcount + 1
    mnum = mnum + 2
   enddo
```

```
    mline = mline + 1
  endif
  endif
  @ mline,0 say replicate("-",80)
  select a
  mline = mline + 1
  skip
 else
  @ mline,0 say "no ekg or cxr data available from that visit"
@ mline + 1,0 say "office date:" + dtoc(notify1->date) + " INVOICE:" +
notify1->invoice + " status:" + mstatus + " prim.off.dx.:" + mdes
  mline = mline + 2
  select a
  skip
 endif
 enddo
enddo
close databases
return
msysdate = ctod("05/01/87")
store ctod(" / / ") to mdate
mtitle1 = "CHRONIC PROBLEM specialty(referral) data for"
mtitle2 = "unstable cardiac patients(all categories)"
set device to print
select a
use notify1 index patient
append from notify for msysdate - date >= 14 .and. substr(category,6,1)
$   "IJKLMNOP"  .and.  substr(category,3,1)  <>  "1"  .and.
substr(condition,2,1) = "H" .and. code = "f"
goto top
reindex
select b
use specalst index patdats
select c
use er_list index erlcode
select d
use chrmedli index chrcode
select a
goto top
do while .not. eof()
 @ 1,(85 - len(mtitle1))/2 say mtitle1
 @ 2,(85 - len(mtitle2))/2 say mtitle2
 @ 3,0 say replicate("=",80)
```

```
store pt_id to mpt_id
@ 4,0 say "PATIENT ID:" + mpt_id + " CLINICAL CATEGORY(prim.dx.):"
+ substr(category,1,1)
@ 5,0 say replicate("=",80)
mline = 6
do while pt_id = mpt_id
 do case
  case substr(category,3,1) = "2"
   store "2(mild sx.)" to mstatus
  case substr(category,3,1) = "3"
   store "3(sev. sx.)" to mstatus
  case substr(category,3,1) = "4"
   store "4(imprvmnt)" to mstatus
  case substr(category,3,1) = "5"
   store "5(hospital)" to mstatus
 endcase
 msugg = space(8)
 store condition to mcondition
 select d
 seek mcondition
 store descript to mdes
 select b
 seek mpt_id + dtoc(notify1->date)
 if found()
  do while pt_id = mpt_id .and. daterequest = notify1->date
 store suggestion to msugg
 store ltrim(msugg) to msugg1
 store rtrim(msugg) to msugg2
 store datedone to ddate
 store datereturn to rdate
 store condition to mconds
 store specialty to mspec
 if mline >= 56
  @ 1,0 say
  @ 2,0 say
  @ 3,0 say replicate
  @ 4,0 say "PATIENT " + pt_id + "(continued)
  @ 5,0 say replicate("-",80)
  mline = 6
 endif
 if substr(mconds,1,1) $ "ABC"
  select d
  seek mconds
```

```
   store descript to mdes1
  else
   select c
   seek mconds
   store descript to mdes1
  endif
  @ mline,0 say "original primary care off. date" + ":" +
dtoc(notify1->date)
  @ mline + 1,0 say "STATUS:" + mstatus + " PRIM.off.dx:" +
rtrim(mdes)
  mline = mline + 2
  mcount = 1
  mnum = 1
  restore from sptype additive
  @ mline,0 say rtrim(sp&mspec) + " office date:" +
dtoc(specalst->datedone) + " INVOICE:" + specalst->invoice
  @ mline + 1,0 say sp&mspec + " recommendations"
  mline = mline + 2
  restore from spresult additive
  do while mcount <= len(msugg2)
   if mcount = 1
    mcol = 0
   endif
   if mcount = 2
    mcol = 30
   endif
   if mcount > 2 .and. mcount <= 6
    if mcount = 3
     mline = mline + 1
     mcol = 0
    endif
    if mcount = 4
     mcol = 30
    endif
    if mcount = 5      mline = mline + 1
     mcol = 0
    endif
    if mcount = 6
     mcol = 30
    endif
   endif
   if mcount > 6
    if mcount = 7
```

```
       mline = mline + 1
       mcol = 0
      endif
      if mcount = 8
       mcol = 30
      endif
     endif
     store substr(msugg2,mnum,1) to mv
     @ mline,mcol say sp&mv
     mcount = mcount + 1
     mnum = mnum + 1
    enddo
    @ mline + 1,0 say rtrim(sp&mspec) + " dx:" + rtrim(mdes1)
    if dtoc(rdate) = (" / / ")
     @ mline + 1,42 say "no re-evaluation indicated"
    else
     @ mline + 1,42 say "return date:" + dtoc(rdate)
    endif
    @ mline + 2,0 say replicate("-",80)
    mline = mline + 3
    select b
    skip
   enddo
   @ mline,0 say replicate("-",80)
   mline = mline + 1
   select a
   skip
  else
   @ mline,0 say "DATA ERROR,office visit from date:" +
dtoc(notify1->date) + " invoice:" + notify1->invoice
   @ mline + 1,0 say "has consult indicated,but no matching specialist
record found"
   @ mline + 2,0 say replicate("-",80)
   @ mline + 3,0 say replicate("-",80)
   mline = mline + 4
    select a
   skip
   endif
  enddo
 enddo
 close databases
 return
```

Stored Variables

Title: LUNG.MEM

Structure/Contents

| | | | |
|---|---|---|---|
| LUN1 | pub | C | "within normal limits" |
| LUN2 | pub | C | "mod(r)lung infiltrate" |
| LUN3 | pub | C | "mod(l)lung infiltrate" |
| LUN4 | pub | C | "bilateral infiltrates" |
| LUN5 | pub | C | "ext. infiltrates(r+l)" |
| LUN6 | pub | C | "ext. infiltrates(r)" |
| LUN7 | pub | C | "ext. infiltrates(l)" |
| LUN8 | pub | C | "single lesion(r)" |
| LUN9 | pub | C | "single lesion(l)" |
| LUN10 | pub | C | "incr pulm vasc" |
| LUN11 | pub | C | "prob.pul edema" |
| LUN12 | pub | C | "bilat. cardiomegaly" |
| LUN13 | pub | C | "left vent.hyper" |
| LUN14 | pub | C | "right vent.hyper" |
| LUN15 | pub | C | "exit this routine" |

15 variables defined, 296 bytes used
241 variables available, 5704 bytes available Stored Variables Title: HEART.MEM Structure/Contents

| | | | |
|---|---|---|---|
| CAR1 | pub | C | "within normal limits" |
| CAR2 | pub | C | "shortened pr interval" |
| CAR3 | pub | C | "prolonged pr interval" |
| CAR4 | pub | C | "chr. ant. wall ischemia" |
| CAR5 | pub | C | "chr.lat.wall ischemia" |
| CAR6 | pub | C | "chr. inf. wall ischemia" |
| CAR7 | pub | C | "biventricular hypertropy" |
| CAR8 | pub | C | "pvc's multifocal" |
| CAR9 | pub | C | "pvc's unifocal" |

| | | |
|---|---|---|
| CAR10 | pub C | "flattened t waves" |
| CAR11 | pub C | "u waves" |
| CAR12 | pub C | "acute ant. wall isch." |
| CAR13 | pub C | "acute inf. wall isch." |
| CAR14 | pub C | "acute lat. wall isch." |
| CAR15 | pub C | "exit this routine" |

15 variables defined, 317 bytes used
241 variables available 5683 bytes available Stored Variables Title: SPRESULT.MEM Structure/Contents

| | | |
|---|---|---|
| SP1 | pub C | "continue with present rx" |
| SP2 | pub C | "med addition" |
| SP3 | pub C | "change exsisting meds" |
| SP4 | pub C | "med deletions" |
| SP5 | pub C | "diet/opc rx" |
| SP6 | pub C | "condition stable" |
| SP7 | pub C | "hospitalization" |
| SP8 | pub C | "more lab tests" |
| SP9 | pub C | "surg.is indicated" |

9 variables defined, 160 bytes used
247 variables available 5840 bytes available Stored Variables Title: SPTYPE.MEM Structure/Contents

| | | |
|---|---|---|
| SPC | pub C | "cardiologist" |
| SPU | pub C | "urologist" |
| SPN | pub C | "neurologist" |

| | | | |
|---|---|---|---|
| SPG | pub | C | "gastroenterologist" |
| SPL | pub | C | "pulmonologist" |
| SPH | pub | C | "hematologist" |
| SPP | pub | C | "psychiatrist" |
| SPR | pub | C | "rhuematologist" |

8 variables defined, 117 bytes used
248 variables available, 5883 bytes available

SAMPLE DATA: ER_ROOM.DBF

| DOCTOR | PT_ID | INVOICE | DATE | DIAGNOSIS | CONDITION | MEDICATION | STATUS | COMPLAINT1 | COMPLAINT2 | FINDING1 | FINDING2 |
|---|---|---|---|---|---|---|---|---|---|---|---|
| hampton | 454-12-3621 | E00000 | 01/26/87 | mb0000 | b | | 1 | nc011 | | | |
| costello | 152-43-2916 | E00001 | 03/01/87 | mc0002 | b | | 1 | np009 | nz026 | | |
| abbott | 011-35-3777 | E00002 | 02/04/87 | mc0002 | b | | 1 | np009 | nc015 | | |
| | 324-53-0764 | E00003 | 03/25/87 | AH0002 | | | 1 | | | | |

SAMPLE DATA: NOTIFY.DBF

| DOCTOR | PT_ID | INVOICE | CATEGORY | CODE | DATE | HINVOICE | EINVOICE | TINVOICE | LINVOICE | SINVOICE | CONDITION |
|---|---|---|---|---|---|---|---|---|---|---|---|
| | 013-32-5312 | O00001 | BE3S K | f | 03/19/87 | | | | | | BH0012 |
| | 013-32-5312 | O00011 | BE2S Lr | f | 03/21/87 | | | | | | BH0012 |
| | 112-23-3145 | O00007 | BE2H P | f | 03/25/87 | | | | | | BH0011 |
| | 112-23-3145 | O00014 | BF5U Iu | f | 03/28/87 | | | | | | BH0011 |
| | 114-24-3145 | O00002 | AE5S Mr | f | 03/27/87 | | | | | | AH0001 |
| | 131-25-6721 | O00012 | AE4S O | f | 03/09/87 | | | | | | AH0000 |
| | 131-25-6721 | O00027 | AE2U Jr | f | 03/27/87 | | | | | | AH0000 |
| | 212-32-5487 | O00008 | AE1U B | f | 01/02/87 | | | | | | AA0005 |
| | 212-32-5487 | O00024 | AE2U A | f | 01/17/87 | | | | | | AA0005 |
| | 212-32-5487 | O00029 | AE3S L | f | 03/19/87 | | | | | | AH0001 |
| | 212-32-5487 | O00032 | AE4S Hu | f | 03/26/87 | | | | | | AH0001 |
| | 152-43-2916 | O00003 | AE5S A | f | 01/13/87 | | | | | | AH0001 |
| | 152-43-2916 | O00010 | AE3U N | t | 01/17/87 | | | | | | AH0010 |
| | 152-43-2916 | O00016 | BE4S Mu | f | 03/22/87 | | | | | | BH0011 |

| | | | | | | | |
|---|---|---|---|---|---|---|---|
| 324-53-0764 | O00004 | AE1S A | | 01/10/87 | | | AH0005 |
| 324-53-0764 | O00033 | AE2U O | t | 01/19/87 | | | AH0005 |
| 324-53-0764 | O00036 | AE3S O | f | 03/19/87 | | | AH0001 |
| 324-53-0764 | O00038 | AE4S M | f | 03/20/87 | | | AR0003 |
| 324-53-0764 | O00046 | AE5S Jr | f | 04/06/87 | | | AH0001 |
| 013-32-6721 | O00000 | BE2U L | f | 03/09/87 | | | BH0012 |

SAMPLE DATA: NOTIFY.DBF

| COMLAINT1 | FINDING 1 | COMPLAINT2 | FINDING2 | | KINVOICE |
|---|---|---|---|---|---|

SAMPLE DATA: SPECALST.DBF

| PT_ID | DATEREQEST | DATEDONE | DATERETURN | INVOICE | INVOICEFRM | CONDITION | SUGGESTION | SPECIALTY |
|---|---|---|---|---|---|---|---|---|
| 013-32-6721 | 03/09/87 | 03/09/87 | | S00000 | O00000 | AH0000 | 4568 | C |
| 013-32-5312 | 03/19/87 | 03/22/87 | 03/29/87 | S00003 | O00001 | H10004 | 236 | C |
| 013-32-5312 | 03/19/87 | 03/29/87 | | S00010 | O00001 | BH0012 | 15826 | C |
| 212-32-5487 | 03/19/87 | 03/22/87 | | S00014 | O00029 | AH0001 | 15 | C |
| 152-43-2916 | 03/22/87 | 03/25/87 | | S00011 | O00016 | BH0011 | 126 | C |
| 324-53-0764 | 03/19/87 | 03/22/87 | 03/27/89 | S00020 | O00036 | H10003 | 28 | C |
| 324-53-0764 | 03/19/87 | 03/29/87 | | S00026 | | AH0001 | 168 | C |
| 112-23-3145 | 03/25/87 | 03/27/87 | | S00009 | O00007 | BH0011 | 126 | C |
| 013-32-5312 | 04/03/87 | 04/05/87 | | S00027 | | AH0001 | 25 | R |
| 324-53-0764 | 04/06/87 | 04/09/87 | | S00034 | O00046 | BG0023 | 16 | H |
| 114-24-3145 | 03/27/87 | 03/28/87 | 04/02/87 | S00009 | O00002 | H10004 | 2356789 | C |
| 114-24-3145 | 03/27/87 | 04/02/87 | 04/13/87 | S00013 | | H10004 | 23 | C |
| 114-24-3145 | 03/27/87 | 04/13/87 | | S00016 | | AH0001 | 16 | C |
| 131-25-6721 | 03/09/87 | 03/12/87 | | S00007 | O00012 | AH0000 | 245 | C |
| 131-25-6721 | 03/27/87 | 03/29/87 | | S00007 | O00027 | G30026 | 2456 | G |

SAMPLE DATA: EKGREC.DBF

| PT_ID | DATEREQEST | DATEDONE | INVOICE | INVOICEFRM | PARAFIELD | DIAGFIELD |
|---|---|---|---|---|---|---|
| 013-32-5312 | 03/19/87 | 03/22/87 | O00000 | | A2U | 4 712 |
| 013-32-5312 | 03/21/87 | 03/23/87 | O00011 | | S1I | 2 611 |

| | | | |
|---|---|---|---|
| 112-32-3145 | 03/25/87 | O00007 | A2I 3 6 7 |
| 112-23-3145 | 03/28/87 | O00014 | A3N 2 4 6 |
| 114-24-3145 | 03/27/87 | O00002 | T A |
| 131-25-6721 | 03/21/87 | O00012 | A 3 4 5 6 |
| 131-25-6721 | 03/27/87 | O00027 | A2U 2 5 7 |
| 212-325-5487 | 03/29/87 | O00029 | A3U 2 411 |
| 212-325-5487 | 03/26/87 | O00032 | A1I 2 512 |
| 324-53-0764 | 03/20/87 | O00036 | C1U 101112 |
| 324-53-0764 | 03/22/87 | O00041 | S1P 3 712 |

SAMPLE DATA: ER_LIST.DBF

| CODETYPE | CODE | DESCRIPT |
|---|---|---|
| H1 | 0000 | acute mi |
| H1 | 0002 | chf,acute, |
| H1 | 0003 | angina,no ischemia |
| H1 | 0004 | early chf |
| V1 | 0005 | acute thrombosis,legs |
| R3 | 0030 | acute low back pain |
| G1 | 0006 | acute abdomen |
| N1 | 0010 | acute cva |
| N2 | 0011 | tia,intermittent |
| V2 | 0013 | malignant hypertension |
| V3 | 0019 | hypertension,mild |
| L1 | 0007 | r/o acute pulm embolus |
| L1 | 0008 | acute pulm insufficiency |
| L3 | 0023 | chronic bronchitis |
| L2 | 0016 | acute asthma |
| E2 | 0012 | ketosis + hyperglycemia |
| E3 | 0015 | hyperglycemia,glyceruria |

List Continued...>

| CODETYPE | CODE | DESCRIPT |
|---|---|---|
| L2 | 0017 | pneumonia |
| I1 | 0014 | septicemia,hypotension |
| G2 | 0018 | portal hypertsn,chirrosis |
| G1 | 0001 | peritonitis |
| G2 | 0020 | ugi bleed,hypotension |
| L3 | 0028 | uri,no sputum |
| G2 | 0022 | lgi bleed |
| G3 | 0026 | gastritis,mild |
| K1 | 0009 | acute urinary obstruction |
| K2 | 0027 | bacteuria,heavy |
| K3 | 0025 | weak urinary stream |
| I2 | 0021 | fever,malaise,anorexia |
| R2 | 0024 | acute polyarthritis |
| I3 | 0029 | functional disorder |

SAMPLE DATA: CXRREC.DBF

| PT_ID | DATEREQEST | DATEDONE | INVOICEFRM | PARAFIELD | DIAGFIELD |
|---|---|---|---|---|---|
| 131-25-6721 | 03/20/87 | 03/22/87 | O00012 | A1U | 2 5 |
| 131-25-6721 | 03/27/87 | 03/27/87 | O00027 | A1W | 2 411 |
| 013-32-5312 | 03/19/87 | 03/21/87 | O00000 | S2W | 2 41113 |
| 013-32-5312 | 03/21/87 | 03/22/87 | O00011 | S2I | 2 |

| DOCTOR | | | |
|---|---|---|---|
| 324-53-0764 | 03/19/87 | 03/22/87 | A2U O00036 |
| 112-23-3145 | 03/25/87 | 03/26/87 | A3U O00007 |
| 112-23-3145 | 03/28/87 | 03/29/87 | A2N O00014 |
| 212-32-5487 | 03/19/87 | 03/21/87 | S O00029 |
| 212-32-5487 | 03/26/87 | 03/27/87 | T O00032 |
| 114-24-3145 | 03/27/87 | 03/29/87 | A2U O00002 |

SAMPLE DATA: NOTIFY1.DBF

| PT_ID | INVOICE | CATEGORY | CODE | DATE | HINVOICE | EINVOICE | TINVOICE | LINVOICE | SINVOICE | CONDITION |
|---|---|---|---|---|---|---|---|---|---|---|
| 013-32-5312 | O00001 | BE3S K | f | 03/19/87 | | | | | 3 6 | BH0012 |
| 013-32-5312 | O00011 | BE2S Lr | f | 03/21/87 | | | | | 2 3 | BH0012 |
| 112-23-3145 | O00007 | BE2H P | f | 03/25/87 | | | | | | BH0011 |
| 112-23-3145 | O00014 | BF5U Iu | f | 03/28/87 | | | | | 3 6 9 | BH0011 |
| 114-24-3145 | O00002 | AE5S Mr | f | 03/27/87 | | | | | 2 3 1112 | AH0001 |
| 131-25-6721 | O00012 | AE4S O | f | 03/09/87 | | | | | | AH0000 |
| 131-25-6721 | O00027 | AE2U Jr | f | 03/27/87 | | | | | A | AH0000 |
| 212-32-5487 | O00029 | AE3S L | f | 03/19/87 | | | | | 1113 | AH0001 |
| 152-43-2916 | O00016 | BE4S Mu | f | 03/22/87 | | | | | | BH0011 |
| 324-53-0764 | O00036 | AE3S O | f | 03/19/87 | | | | | | AH0001 |
| 324-53-0764 | O00046 | AE5S Jr | f | 04/06/87 | | | | | | AH0001 |
| 013-32-6721 | O00000 | BE2U L | f | 03/29/87 | | | | | | BH0012 |

SAMPLE DATA: ABN_LABA.DBF

| SED_RATE | POTTASIUM | BLD_SUG | PH | PO2 | PCO2 | WBC | CALCIUM | EKG | CXR |
|---|---|---|---|---|---|---|---|---|---|
| A1N19.0 | A2W5.0 | | | | | A4P3.5 | A1U12.6 | T A | T |
| A1W45 | | | | | | | | A1P | |
| S2W17.4 | | | | | | | | | |
| A2W27.8 | T C | A1N432 | | | | | | A2I | |
| S2I30.7 | A1P5.3 | | | | | A4U2.9 | | | T C |
| A2I28 | A3W3.2 | | | | | | | | T |
| A2U24.7 | | | | | | A2I22.2 | | | A2W |
| A2I24 | | | A3N6.9 | | | | | S2U | S1W |
| S2I20.5 | A4N2.9 | | | | | A2W12.8 | A2N14.8 | | |
| A2N22.9 | C3N6.9 | | | | S2N55 | C2N14.7 | | | S1N |
| S2I22.9 | | | | | | S2I14.0 | | | A1W |
| S1W30.5 | | | | | | C4W4.3 | | | A2U |
| S1U17.4 | A1N5.2 | | | | | A2N13.6 | | T C | |
| A1W20.4 | A2U5.9 | | | | | A1W16.8 | | A#U | A3U |
| | S1U4.3 | | | | | | | | |

SAMPLE DATA: CHRMEDLI.DBF

| CODETYPE | CODE | DESCRIPT |
|---|---|---|
| AH | 0000 | ACUTE ANGINA,UNSTABLE,CHF |
| AH | 0001 | ACUTE ANGINA,UNSTABLE |
| AR | 0002 | SYST.LUPUS + NEPHRITIS |
| AR | 0003 | PROG.SYST.SCLEROSIS,UREMI |
| AV | 0007 | MALIGNT.HYPERTENS.(SYMPT) |
| AL | 0010 | COPD,SEVERE HYPERCAPNIA |
| AV | 0006 | CLAUDICATION,REST,CALF |
| AN | 0009 | HYPERTENSIVE TIA |
| AP | 0004 | ACUTE BLASTOCYT.LEUKEMIA |
| AC | 0005 | METASTATIC CA + CHEMOTH. |
| AI | 0008 | AUTOIMM.DEFIENCY SYNDROME |
| BG | 0013 | ULCERATIVE COLITIS |
| BH | 0011 | CHRONIC ANGINA |
| BH | 0012 | CHF,CHR.VENT.HYPERTROPHY |
| BN | 0015 | CVA,RECENT |
| BK | 0016 | ACUTE GLOMERULONEPHRITIS |
| BE | 0019 | DIABETES MELLITUS |
| BL | 0018 | COPD,MILD HYPERCAPNIA |
| BV | 0017 | CHRONIC CLAUDICATION |
| BP | 0014 | MULTIPLE MYELOMA |
| BR | 0020 | ACUTE GOUTY ARTHRITIS |
| BR | 0022 | ACUTE RHUEMATOID ARTHR. |

| CODETYPE | CODE | DESCRIPT |
|---|---|---|
| BG | 0023 | CHR.PANCREATITIS |
| CH | 0024 | CARDIOMEGALY,ASYMPT.RHD |
| BK | 0021 | CHRONIC PYELONEPHRITIS |
| CP | 0025 | PERNICOUS ANEMIA |
| CP | 0026 | IRON DEF.ANEMIA |
| CK | 0027 | CHRONIC RENAL STONES |
| CR | 0028 | OSTEOARTH.,SEVERE |
| CG | 0029 | CHRONIC PEPTIC ULCER |
| CL | 0030 | CHRONIC BROCHITIS |

List Continued...>

SAMPLE DATA: ABN_LABA.DBF

| DOCTOR | PT_ID | DATEREQEST | DATEDONE | INVOICE | INVOICEFRM | BUN | CR | HG | H(T |
|---|---|---|---|---|---|---|---|---|---|
| abbott | 011-35-3777 | 01/09/87 | 01/09/87 | L00007 | O00005 | C2U29.6 | C2U4.3 | A2I11.4 | C(U29.4 |
| abbott | 011-35-3777 | 01/14/87 | 01/14/87 | L00010 | O00010 | A1N21.0 | A2W5.2 | S3U10.2 | C(U32.5 |
| abbott | 011-35-3777 | 01/21/87 | 01/22/87 | L00017 | O00011 | | C2U56 | | C1I29.1 |
| abbott | 011-35-3777 | 02/14/87 | 02/14/87 | L00019 | O00015 | | S3W40 | | C2U30.5 |
| abbott | 011-35-3777 | 01/14/87 | 01/15/87 | L00000 | O00007 | | | T B | T B |
| abbott | 131-25-6721 | | | L00005 | O00009 | T B | T C | A1I9.9 | A2N28.5 |
| abbott | 131-25-6721 | | | L00009 | O00012 | | C2I36.5 | T B | |
| abbott | 131-25-6721 | | | L00002 | O00004 | S2I28.7 | A1U5.3 | S3U9.8 | |
| abbott | 212-32-5487 | | | L00004 | O00008 | S2I15.6 | A1W4.3 | C4W7.9 | |
| abbott | 212-32-5487 | | | L00018 | O00024 | A2W12.4 | | S1U10.5 | S3N27.4 |

SAMPLE DATA: NOTIFY1.DBF

| COMPLAINT1 | FINDING1 | | | | | | |
|---|---|---|---|---|---|---|---|
| hampton | 010-53-6677 | | | | L00001 | O00000 | A2N12.0 |
| hampton | 010-53-6677 | | | | L00014 | O00019 | A2I10.3 |
| hampton | 010-53-6677 | | | | L00022 | O00025 | A1U10.6 A2N24.1 S2N29.9 |
| hampton | 454-12-3621 | | | | L00003 | O00002 | S2P9.2 C4U30.2 |
| hampton | 454-12-3621 | | | | L00011 | O00006 | S2U10.4 S1.31.7 |
| hampton | 454-12-3621 | | | | L00013 | O00014 | S2U9.8 S2U21.0 A2U32.6 |
| hampton | 011-35-3777 | 03/28/87 | 03/29/87 | | L00016 | S00011 | |
| hampton | 131-25-6721 | 03/08/87 | 03/13/87 | | L00017 | O00031 | a |
| | | | | | L00018 | | |

SAMPLE DATA: ENCOUNTF.DBF

| DOCTOR | PT_ID | INVOICE | DATE | COMPLAINT2 | FINDING2 | KINVOICE | TYPE | STATUS | PRIM_DX | SEC_DX | TERT_DX | NEW_MED | MEI_CHANGE | LAB_WORK |
|---|---|---|---|---|---|---|---|---|---|---|---|---|---|---|
| abbott | 011-35-3777 | O00005 | 01/14/87 | | | | s | 2 | AH0001 | | | 0 | 0 | 1 |
| abbott | 011-35-3777 | O00003 | 01/09/87 | | | | s | 3 | AH0001 | | | 0 | 1 | 0 |
| abbott | 011-35-3777 | O00010 | 01/21/87 | | | | s | 1 | AH0001 | | | 0 | 0 | 1 |
| abbott | 011-35-3777 | O00011 | 02/14/87 | | | | s | 1 | AH0001 | | | 0 | 0 | 1 |
| abbott | 011-35-3777 | O00015 | 02/17/87 | | | | s | 1 | AH0001 | | | 0 | 1 | 1 |
| abbott | 212-32-5487 | O00004 | 01/09/87 | | | | s | 2 | AR0002 | CK0027 | | 0 | 0 | 1 |
| hampton | 454-12-3621 | O00014 | 02/01/87 | | | | s | 1 | AC0005 | BH0012 | BG0023 | 0 | 1 | 1 |
| abbott | 131-25-6721 | O00007 | 01/02/87 | | | | U | 5 | BG0013 | BV0017 | BR0020 | 0 | 1 | 0 |
| abbott | 131-25-6721 | O00009 | 01/14/87 | | | | s | 1 | BG0013 | BV0017 | BR0020 | 0 | 0 | 1 |
| abbott | 131-25-6721 | O00012 | 01/20/87 | | | | U | 2 | BG0013 | BV0017 | BR0020 | 0 | 0 | 0 |
| abbott | 131-25-6721 | O00027 | 02/27/87 | | | | U | 1 | BG0013 | BV0017 | BR0020 | 0 | 0 | 1 |
| abbott | 212-32-5487 | O00031 | 03/08/87 | | | | s | 1 | AR0002 | | | 0 | 1 | 1 |
| abbott | 212-32-5487 | O00008 | 01/13/87 | | | | s | 1 | AR0002 | | | 0 | 1 | 1 |
| abbott | 212-32-5487 | O00024 | 02/17/87 | | | | s | 1 | AR0002 | | | 0 | 0 | 0 |
| abbott | 212-32-5487 | O00029 | 02/25/87 | | | | s | 3 | AR0002 | | | 0 | 0 | 1 |
| abbott | 212-32-5487 | O00032 | 03/09/87 | | | | s | 1 | AR0002 | | | 0 | 0 | 1 |
| hampton | 010-53-6677 | O00000 | 01/01/87 | | | | s | 1 | AC0005 | BE0019 | CK0026 | 0 | 0 | 1 |
| hampton | 010-53-6677 | O00016 | 01/17/87 | | | | U | 3 | AC0005 | BE0019 | CK0026 | 0 | 0 | 0 |
| hampton | 010-53-6677 | O00019 | 02/02/87 | | | | s | 1 | AC0005 | BE0019 | CK0026 | 0 | 0 | 0 |
| hampton | 010-53-6677 | O00025 | 02/09/87 | | | | s | 1 | AC0005 | BE0019 | CK0026 | 0 | 0 | 1 |
| hampton | 010-53-6677 | O00030 | 02/27/87 | | | | s | 1 | AC0005 | BE0019 | CK0026 | 0 | 0 | 0 |
| hampton | 324-53-0764 | O00001 | 01/10/87 | | | | s | 1 | AP0004 | | | 0 | 0 | 0 |
| hampton | 324-53-0764 | O00033 | 01/19/87 | | | | s | 1 | AP0004 | | | 0 | 0 | 1 |
| hampton | 324-53-0764 | O00036 | 03/19/87 | | | | s | 1 | AP0004 | | | 0 | 0 | 0 |
| hampton | 324-53-0764 | O00038 | 03/26/87 | | | | s | 4 | AP0004 | | | 0 | 0 | 0 |

| | | | | | | |
|---|---|---|---|---|---|---|
| hampton | 324-53-0764 | O00041 | 04/01/87 | s | 1 | AP0004 |
| hampton | 454-12-3621 | O00002 | 01/08/87 | U | 1 | AC0005 BH0012 BG0023 |
| hampton | 454-12-3621 | O00006 | 01/23/87 | s | 1 | AC0005 BH0012 BG0023 |

SAMPLE DATA: ENCOUNTF.DBF

| CONSULT | NEWPROBLEM | INJECTION | CONDITION | WEIGHT | SYSTOLIC | DIASTOLIC |
|---|---|---|---|---|---|---|
| 0 | 0 | 0 | AH0001 | 0 | 135 | 95 |
| 0 | 0 | 0 | AH0001 | 0 | 175 | 100 |
| 0 | 0 | 0 | AH0001 | 0 | | |
| 0 | 0 | 0 | AH0001 | 0 | | |
| 0 | 0 | 0 | AH0001 | 0 | | |
| 0 | 0 | 0 | AR0002 | 0 | | |
| 0 | 0 | 0 | BG0023 | 0 | | |
| 0 | 0 | 0 | BG0013 | 0 | | |
| 0 | 0 | 0 | BG0013 | 0 | | |
| 0 | 0 | 0 | BG0013 | 0 | 160 | 90 |
| 0 | 0 | 0 | BG0013 | 0 | 169 | 90 |
| 0 | 0 | 0 | BG0013 | 0 | 160 | 95 |
| 0 | 0 | 0 | AR0002 | 0 | | |
| 0 | 0 | 0 | AR0002 | 0 | | |
| 0 | 0 | 0 | AR0002 | 0 | | |
| 0 | 0 | 0 | AC0005 | 0 | 140 | 90 |
| 0 | 0 | 0 | BE0019 | 0 | 155 | 95 |
| 0 | 0 | 0 | BE0019 | 0 | 145 | 95 |
| 0 | 0 | 0 | CK0026 | 0 | 140 | 90 |
| 0 | 1 | 0 | BE0019 | 0 | 150 | 90 |
| 0 | 0 | 0 | AP0004 | 0 | | |
| 0 | 0 | 0 | AP0004 | 0 | | |
| 0 | 0 | 0 | AP0004 | 0 | | |
| 0 | 0 | 0 | AP0004 | 0 | | |
| 0 | 0 | 0 | AP0004 | 0 | 160 | 90 |
| 0 | 0 | 0 | BH0012 | 0 | 160 | 90 |
| 0 | 0 | 0 | AC0005 | 0 | 150 | 89 |

SAMPLE DATA: ENCOUNT1.DBF

| COMPLAINT1 | COMPLAINT2 | FINDING1 | FINDING2 |
|---|---|---|---|
| HA002 | | HA001 | HA002 |
| IB029 | IB023 | IB013 | IB018 |
| IB022 | | LC023 | |

| | | | |
|---|---|---|---|
| HA000 | | | |
| RB014 | | RA022 | HA000 |
| LA016 | HA000 | LA011 | HA000 |
| LC021 | | | IB025 |
| | | | |
| GC020 | | GB020 | |
| | | | |
| HA001 | HA002 | HB002 | |
| HA002 | IB022 | RA022 | IA024 |
| RB014 | | | |
| | | | |
| NA007 | | NA007 | |
| NA007 | | NA008 | |
| | | | |
| HB026 | HB004 | HB002 | HB004 |
| | | | |
| IB029 | IB022 | IA024 | IA024 |
| IB022 | | IB025 | IB018 |
| LC021 | | IA024 | |
| IB029 | | | |

I claim:

1. A computer data entry routine for entering and storing either electrocardiographic (EKG) or chest x-ray (CXR) test results from a lab test request document in a primary care out-patient setting, including:
   means for loading first patient data into the computer to create a data record, said first patient data reflecting EKG or CXR diagnostic abnormalities,
   means for defining a plurality of data fields for use in identifying said data record,
   means for recalling previously entered test result data pertaining to said EKG or CXR test currently being entered to accompany as compiled, encoded parameter data the current said EKG or CXR test results in said data record,
   means for automatically transferring said parameter data into a master lab record assigned to said patient, said transferring occurring concurrently with the creation of said data record,
   means for identifying the circumstance which prevailed at the time the lab test request was made, said identified circumstance dictating the manner in which the data record is referenced at a later point in time.

2. The entry routine of claim 1 wherein the means for loading includes:
   means for generating a menu listing of a plurality of standard EKG or CXR abnormalities, including a selection signifying that no abnormality is present,
   means for selecting up to a prescribed number of abnormalities from the menu listing,
   means for storing the selections as numbered subscripts.

3. The entry routine of claim 1 further including:
   means for entering patient identification number, date which the lab test request was ordered and date in which the lab test request was finished as a means for identifying said EKG or CXR data record to be created,
   and wherein said means for identifying the circumstance includes means for specifying whether the lab test request was ordered during a formal encounter or an informal encounter, said formal encounter including an office visit, emergency room visit or specialist visit, and said informal encounter including all other encounters.

4. The entry routine of claim 1 wherein the means for recalling further includes:
   means for examining said patient's prior EKG or CXR data records and extracting data, said data including a date and amount of a first abnormality, a date and amount of a last abnormality, most recent result entered (normal or abnormal), and an indication of whether a test has been consistently normal or abnormal.

5. The entry routine of claim 1 wherein the means for transferring includes:
   means for testing whether a master lab record already exists or not,
   means for creating the master lab record if said testing means determines that one does not already exist, and for transferring parameter data and patient identifying data to said newly created lab record,
   means for only sending said parameter data if said testing means determines that a master lab record already exists.

6. An entry routine for entering and storing blood test data from a lab test request document in a primary care out-patient setting, including:
   means for identifying the circumstance which prevailed at the time the lab test request was made, wherein said means for identifying includes means for specifying whether the lab test request was ordered during a formal encounter or an informal encounter, said formal encounter including an office visit, emergency room visit or specialist visit, and said informal encounter including all other encounters,
   means for determining whether or not a previous master record exists, said previous master record having been created by the prior running of a separate electrocardiographic EKG or chest x-ray CXR routine, or through the prior entry of blood test data,
   means for determining prior test results for accompanying as compiled, encoded parameter data each current blood test result entered, said prior test results including a date and amount of a first abnormality, a date and amount of a last abnormality, a most recent test result and a measure of the consistency of prior results,
   means for activating a customized data entry screen for the entry of blood test results from the lab test request form.

7. For use in a computer medical database system in a primary care out-patient setting, a report generation means for generating reports, said report generation means including a first and second print routines, said report generation means including:
   means for specifying a criterion and selecting records from a database of medical records which meet said criterion,
   means for storing the set of medical records which meet said criterion,
   said first print routine including;
      means for accessing from said stored set electrocardiographic (EKG) and chest x-ray (CXR) test results from EKG and CXR data records which are linked to a preselected primary care office visit from which said tests were ordered, said test results existing as numbered subscripts,
      means for obtaining literal text corresponding to said subscripts, said literal text consisting of descriptions of EKG and CXR abnormalities,
      means for printing out the literal text in conjunction with data recorded during said primary care office visit for each patient in said stored set,
   said second print routine including;
      means for accessing consultant data from specialist records within said stored set which stem from referrals made in a primary care office visit, said consultant data existing as subscripts representing the type of specialist and the recommendations made by the specialist,
      means for obtaining literal text corresponding to said specialist subscripts,
      means for printing said specialist literal text out in conjunction with data recorded during said primary care office visit.

* * * * *